United States Patent
Amara et al.

(10) Patent No.: US 6,451,993 B1
(45) Date of Patent: *Sep. 17, 2002

(54) POLYNUCLEOTIDES ENCODING HUMAN EXCITATORY AMINO ACID TRANSPORTER 4 (EAAT4)

(75) Inventors: Susan G. Amara; Jeffrey L. Arriza; Wendy A. Fairman, all of Portland, OR (US)

(73) Assignee: Oregon Health & Sciences University, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/566,708

(22) Filed: May 9, 2000

Related U.S. Application Data

(60) Division of application No. 09/332,740, filed on Jun. 14, 1999, now Pat. No. 6,060,307, which is a division of application No. 08/663,808, filed on Jun. 14, 1996, now Pat. No. 5,912,171, which is a continuation-in-part of application No. 08/140,729, filed on Oct. 20, 1993, now Pat. No. 5,658,782.

(51) Int. Cl.⁷ .............................................. C07H 21/04

(52) U.S. Cl. ................................................... 536/23.2

(58) Field of Search ........................... 536/23.1, 23.2

(56) References Cited

U.S. PATENT DOCUMENTS

| | | |
|---|---|---|
| 4,683,195 A | 7/1987 | Mullins et al. |
| 4,683,202 A | 7/1987 | Mullins |
| 5,385,831 A | 1/1995 | Mulvihill et al. |
| 5,424,185 A | 6/1995 | Lam et al. |
| 5,882,926 A | 3/1999 | Lam et al. |

OTHER PUBLICATIONS

Fairman et al. An excitatory amino–acid transporter with properties of a ligand–gated chloride channel. Nature (1995) 375:599–693, Jun. 1995.*
Anderson et al., (1989) J. Biol. Chem., 264: p. 8222–8229.
Arriza et al. (1994) J. Neurosci., vol. 14, No. 9, p. 5559–5569.
Arriza et al., (1992) J. Neurosci., 12: 4045–4055.
Barish, (1983) J. Physiol., 342: 309–325.
Bertling et al., (1987) Bioscience Reports, 7: 107–112.
Blakely et al., (1991) Anal. Biochem., 194: 302–308.
Bouvier et al., (1992) Nature, 360: 471–474.
Bussolati et al., (1992) J. Biol. Chem., 267: 8330–8335.
Choi et al., (1987) Neurosci., 7: 357–358.
Chomczynski & Sacchi, (1987) Anal. Biochem., 162: 156–159.
Christensen (1990), Physiol. Rev., 70: 43: 77.
Christensen et al., (1967), J. Biol. Chem., 242: 5237–5246.
Dreyer et al., (1996) Arch. Ophthamol., 114: 299–305.
Eisenberg et al., (1984), J. Molec. Biol., 179: 125–142.
Engelke et al., (1992) J. Bacteriol., 171: 5551–5560.
Felgner et al., (1987) Proc. Natl. Acad. Sci., 84: 7412–7417.
Gerogiou, (1988) AICHE Journal, vol. 34, No. 8, pp. 1233–1248.
Gluzman, (1981) Cell, 23: 175–182.
Guastella et al., (1990) Science, 249: 1303–1306.
Guastella et al., (1992) Proc. Natl. Sci., 89: 7189–7193.
Honda, (1996) Nippon Ganka Gakkst Zasshi, 100: 937–955.
Kalloniatis, (1995) J. Amer. Optom. Assoc., 66: 750–757.
Kanai et al. (1992) Nature, 360: 467–471.
Kanai et al. (1993) Trends in Neurosci., vol. 16, No. 9, p. 365–370.
Kanai et al., (1993) FASEB J., 7: 1450–1459.
Kanai et al., (1994) J. Biol. Chem., vol. 269, No. 32, pp. 20599–20606.
Kanner & Schuldiner, (1987), CRC Crit. Rev. Biochem., 22: 1–38.
Kanner, (1993), FEBS Lett., 325 (1,2): p. 95–99.
Kataoka et al., (1997) J. Neurosci., 17: 7017–7024.
Kavanaugh et al., (1992) J. Biol. Chem., 267: 22007–22009.
Kim et al., (1991) Nature, 352: 725–728.
Kong et al., (1993) J. Biol. Chem., 268: 1509–1512.
Kozak, (1987) Nucleic Acid Res., 15: 8125–8132.
Maenz et al., (1992), J. Biol. Chem., 267: 1510–1516.
Makowske & Christensen, (1982) J. Biol. Chem., 257: 14635–14638.
Nicholls & Atwell, (1990), TIPS, 11: 462–468.
Olney et al., (1990) Science, 248: 596–599.
Pines et al., (1992) Nature, 360: p. 464–467.
Quick and Lester, (1994) Methods in Neuroscience, 19: 261–279.
Saiki et al., (1988) Science, 239: 487–491.
Sanger et al., (1977) Proc. Natl. Acad. Sci., 74: 5463.
Schloss et al. (1992) FEBS Lett., 307 (1): p. 76–80.
Shashidharan et al., (1993), Biochim. Biophys. Acta., 1216: p. 161–164.

(List continued on next page.)

Primary Examiner—Ponnathapu Achutamurthy
Assistant Examiner—Kathleen Kerr
(74) Attorney, Agent, or Firm—McDonnell Boehnen Hulbert & Berghoff

(57) ABSTRACT

The present invention relates to novel mammalian amino acid transporter proteins and the genes that encode such proteins. The invention is directed toward the isolation, characterization and pharmacological use of a human amino acid transporter protein termed EAAT4 and genes encoding such a transporter. The invention specifically provides isolated complementary DNA copies of mRNA corresponding to this transporter gene. Also provided are recombinant expression constructs capable of expressing this amino acid transporter gene in cultures of transformed prokaryotic and eukaryotic cells, as well as such cultures of transformed cells that synthesize the human amino acid transporter protein encoded therein. The invention also provides methods for screening in vitro compounds having transport-modulating properties using preparations of transporter proteins from such cultures of cells transformed with recombinant expression constructs.

2 Claims, 16 Drawing Sheets

OTHER PUBLICATIONS

Sheng et al., (1996) Neuron., 17: 575–578.
Smith & Johnson, (1988) Gene, 67: 31–40.
Smithies et al., (1985) Nature, 317: 230–234.
Stelzner et al., (1993) FASEB J., 7(4/part 2): A575.
Storck et al., (1992), Proc. Natl. Acad. Sci., 89: p. 10955–10959.
Thomas & Capecchi, (1987) Cell, 51: 503–512.
Uhl, (1992), Trends in Neurosci., 15(7): 265–268.
Wallace et al., (1990) J. Bacteriol., 172: 3214–3220.
Wang et al., (1991) Nature, 352: 729–731.
Zerangue et al., (1995) J. Biol. Chem., 270: 6433–6435.

* cited by examiner

```
        10        20        30        40        50        60
         *         *         *         *         *         *
GATAGACCATGAGCAGCCATGGCAACAGCCTGTTCCTTCGGGAGAGCGGCCAGCGGCTGG 70        80        90       100       110       120
         *         *         *         *         *         *
GCCGGGTGGGCTGGCTGCAGCGGCTGCAGGAAAGCCTGCAGCAGAGAGCACTGCGCACGC 130       140       150       160       170       180
         *         *         *         *         *         *
GCCTGCGCCTGCAGACCATGACCCTCGAGCACGTGCTGCGCTTCCTGCGCCGAAACGCCT 190       200       210       220       230       240
         *         *         *         *         *         *
TCATTCTGCTGACGGTCAGCGCCGTGGTCATTGGGGTCAGCCTGGCCTTTGCCCTGCGCC 250       260       270       280       290       300
         *         *         *         *         *         *
CATATCAGCTCACCTACCGCCAGATCAAGTACTTCTCTTTTCCTGGAGAGCTTCTGATGA 310       320       330       340       350       360
         *         *         *         *         *         *
GGATGCTGCAGATGCTGGTGTTACCTCTCATTGTCTCCAGCCTGGTCACAGGTATGGCAT 370       380       390       400       410       420
         *         *         *         *         *         *
CCCTGGACAACAAGGCCACGGGGCGGATGGGGATGCGGGCAGCTGTGTACTACATGGTGA 430       440       450       460       470       480
         *         *         *         *         *         *
CCACCATCATCGCGGTCTTCATCGGCATCCTCATGGTCACCATCATCCATCCCGGGAAGG 490       500       510       520       530       540
         *         *         *         *         *         *
GCTCCAAGGAGGGGCTGCACCGGGAGGGCCGGATCGAGACCATCCCCACAGCTGATGCCT 550       560       570       580       590       600
         *         *         *         *         *         *
TCATGGACCTGATCAGAAATATGTTTCCACCAAACCTTGTGGAGGCCTGCTTCAAACAGT 610       620       630       640       650       660
         *         *         *         *         *         *
TCAAGACGCAGTACAGCACGAGGGTGGTAACCAGGACCATGGTGAGGACAGAGAACGGGT 670       680       690       700       710       720
         *         *         *         *         *         *
CTGAGCCGGGTGCCTCCATGCCTCCTCCATTCTCAGTGGAGAACGGAACCAGCTTCCTGG
```

Figure 1A

```
       730        740        750        760        770        780
        *          *          *          *          *          *
AAAATGTCACTCGGGCCTTGGGTACCCTGCAGGAGATGCTGAGCTTTGAGGAGACTGTAC 790        800        810        820        830        840
        *          *          *          *          *          *
CCGTGCCTGGCTCCGCCAATGGCATCAACGCCCTGGGCCTCGTGGTCTTCTCTGTGGCCT 850        860        870        880        890        900
        *          *          *          *          *          *
TTGGGCTGGTCATTGGTGGCATGAAACACAAGGGCAGAGTCCTCAGGGACTTCTTCGACA 910        920        930        940        950        960
        *          *          *          *          *          *
GCCTCAATGAGGCTATTATGAGGCTGGTGGGCATCATTATCTGGTATGCACCTGTGGGCA 970        980        990       1000       1010       1020
        *          *          *          *          *          *
TCCTGTTCCTGATTGCTGGGAAGATTCTGGAGATGGAAGACATGGCCGTCCTGGGGGGTC 1030       1040       1050       1060       1070       1080
        *          *          *          *          *          *
AGCTGGGCATGTACACCCTGACCGTCATCGTGGGCCTGTTCCTCCATGCCGGCATTGTCC 1090       1100       1110       1120       1130       1140
        *          *          *          *          *          *
TTCCCCTCATCTACTTCCTCGTCACTCACCGGAACCCCTTCCCCTTCATTGGGGGCATGC 1150       1160       1170       1180       1190       1200
        *          *          *          *          *          *
TACAAGCCCTCATCACCGCTATGGGCACGTCTTCCAGCTCGGCAACGCTGCCCATCACCT 1210       1220       1230       1240       1250       1260
        *          *          *          *          *          *
TCCGCTGCCTGGAGGAGGGCCTGGGTGTGGACCGCCGCATCACCAGGTTCGTCCTGCCCG 1270       1280       1290       1300       1310       1320
        *          *          *          *          *          *
TGGGCGCCACGGTCAACATGGATGGCACTGCCCTCTACGAGGCCCTGGCTGCCATCTTCA 1330       1340       1350       1360       1370       1380
        *          *          *          *          *          *
TTGCTCAAGTTAACAACTACGAGCTCAACCTGGGTCAGATCACAACCATCAGCATCACGG 1390       1400       1410       1420       1430       1440
        *          *          *          *          *          *
CCACAGCAGCCAGTGTTGGGCTGCTGGCATCCCCCAGGCGGGTCTGGTCACCATGGTCA
```

Figure 1B

```
      1450       1460       1470       1480       1490       1500
        *          *          *          *          *          *
TTGTGCTTACGTCGGTCGGCTTGCCCACGGAAGACATCACGCTCATCATCGCCGTGGACT 1510       1520       1530       1540       1550       1560
        *          *          *          *          *          *
GGTTCCTTGACCGGCTTCGCACAATGACCAACGTACTGGGGGACTCAATTGGAGCGGCCG 1570       1580       1590       1600       1610       1620
        *          *          *          *          *          *
TCATCGAGCACTTGTCTCAGCGGGAGCTGGAGCTTCAGGAAGCTGAGCTTACCCTCCCCA 1630       1640       1650       1660       1670       1680
        *          *          *          *          *          *
GCCTGGGGAAACCCTACAAGTCCCTCATGGCACAGGAGAAGGGGGCATCCCGGGGACGGG 1690       1700       1710       1720       1730
        *          *          *          *          *
GAGGCAACGAGAGTGCTATGTGAGGGGCCTCCAGCTCTGCCCCCCCAGAGAGGA
```

Figure 1C

```
Met Ser Ser His Gly Asn Ser Leu Phe Leu Arg Glu Ser Gly Gln
             5                    10                   15

Arg Leu Gly Arg Val Gly Trp Leu Gln Arg Leu Gln Glu Ser Leu
            20                    25                   30

Gln Gln Arg Ala Leu Arg Thr Arg Leu Arg Leu Gln Thr Met Thr
            35                    40                   45

Leu Glu His Val Leu Arg Phe Leu Arg Arg Asn Ala Phe Ile Leu
            50                    55                   60

Leu Thr Val Ser Ala Val Val Ile Gly Val Ser Leu Ala Phe Ala
            65                    70                   75

Leu Arg Pro Tyr Gln Leu Thr Tyr Arg Gln Ile Lys Tyr Phe Ser
            80                    85                   90

Phe Pro Gly Glu Leu Leu Met Arg Met Leu Gln Met Leu Val Leu
            95                   100                  105

Pro Leu Ile Val Ser Ser Leu Val Thr Gly Met Ala Ser Leu Asp
           110                   115                  120

Asn Lys Ala Thr Gly Arg Met Gly Met Arg Ala Ala Val Tyr Tyr
           125                   130                  135

Met Val Thr Thr Ile Ile Ala Val Phe Ile Gly Ile Leu Met Val
           140                   145                  150

Thr Ile Ile His Pro Gly Lys Gly Ser Lys Glu Gly Leu His Arg
           155                   160                  165

Glu Gly Arg Ile Glu Thr Ile Pro Thr Ala Asp Ala Phe Met Asp
           170                   175                  180

Leu Ile Arg Asn Met Phe Pro Pro Asn Leu Val Glu Ala Cys Phe
           185                   190                  195

Lys Gln Phe Lys Thr Gln Tyr Ser Thr Arg Val Val Thr Arg Thr
           200                   205                  210

Met Val Arg Thr Glu Asn Gly Ser Glu Pro Gly Ala Ser Met Pro
           215                   220                  225

Pro Pro Phe Ser Val Glu Asn Gly Thr Ser Phe Leu Glu Asn Val
           230                   235                  240

Thr Arg Ala Leu Gly Thr Leu Gln Glu Met Leu Ser Phe Glu Glu
           245                   250                  255
```

Figure 2A

```
Thr Val Pro Val Pro Gly Ser Ala Asn Gly Ile Asn Ala Leu Gly
            260             265             270
Leu Val Val Phe Ser Val Ala Phe Gly Leu Val Ile Gly Gly Met
            275             280             285
Lys His Lys Gly Arg Val Leu Arg Asp Phe Phe Asp Ser Leu Asn
            290             295             300
Glu Ala Ile Met Arg Leu Val Gly Ile Ile Ile Trp Tyr Ala Pro
            305             310             315
Val Gly Ile Leu Phe Leu Ile Ala Gly Lys Ile Leu Glu Met Glu
            320             325             330
Asp Met Ala Val Leu Gly Gly Gln Leu Gly Met Tyr Thr Leu Thr
            335             340             345
Val Ile Val Gly Leu Phe Leu His Ala Gly Ile Val Leu Pro Leu
            350             355             360
Ile Tyr Phe Leu Val Thr His Arg Asn Pro Phe Pro Phe Ile Gly
            365             370             375
Gly Met Leu Gln Ala Leu Ile Thr Ala Met Gly Thr Ser Ser Ser
            380             385             390
Ser Ala Thr Leu Pro Ile Thr Phe Arg Cys Leu Glu Glu Gly Leu
            395             400             405
Gly Val Asp Arg Arg Ile Thr Arg Phe Val Leu Pro Val Gly Ala
            410             415             420
Thr Val Asn Met Asp Gly Thr Ala Leu Tyr Glu Ala Leu Ala Ala
            425             430             435
Ile Phe Ile Ala Gln Val Asn Asn Tyr Glu Leu Asn Leu Gly Gln
            440             445             450
Ile Thr Thr Ile Ser Ile Thr Ala Thr Ala Ala Ser Val Gly Ala
            455             460             465
Ala Gly Ile Pro Gln Ala Gly Leu Val Thr Met Val Ile Val Leu
            470             475             480
Thr Ser Val Gly Leu Pro Thr Glu Asp Ile Thr Leu Ile Ile Ala
            485             490             495
Val Asp Trp Phe Leu Asp Arg Leu Arg Thr Met Thr Asn Val Leu
            500             505             510
Gly Asp Ser Ile Gly Ala Ala Val Ile Glu His Leu Ser Gln Arg
            515             520             525
```

Figure 2B

```
Glu Leu Glu Leu Gln Glu Ala Glu Leu Thr Leu Pro Ser Leu Gly
                530             535                 540

Lys Pro Tyr Lys Ser Leu Met Ala Gln Glu Lys Gly Ala Ser Arg
                545             550                 555

Gly Arg Gly Gly Asn Glu Ser Ala Met
                560         564
```

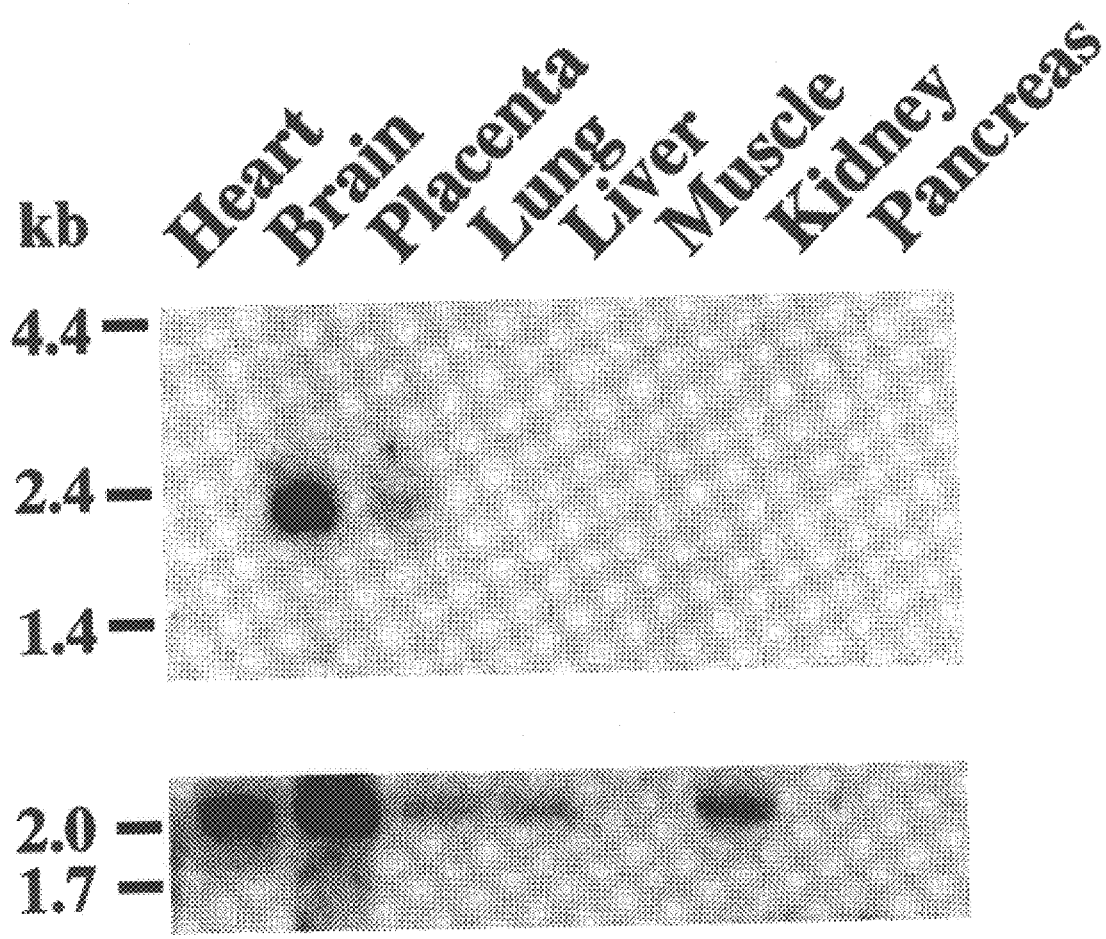

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1734 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 9..1703

(ix) FEATURE:
      (A) NAME/KEY: 5'UTR
      (B) LOCATION: 1..8

(ix) FEATURE:
      (A) NAME/KEY: 3'UTR
      (B) LOCATION: 1704..1734

(xi) SEQUENCE DESCRIPTION: SEQ ID NO:1:

GATAGACC ATG AGC AGC CAT GGC AAC AGC CTG TTC CTT CGG GAG AGC GGC   50

```
            Met Ser Ser His Gly Asn Ser Leu Phe Leu Arg Glu Ser Gly
             1               5                      10

CAG CGG CTG GGC CGG GTG GGC TGG CTG CAG CGG CTG CAG GAA AGC CTG          98
Gln Arg Leu Gly Arg Val Gly Trp Leu Gln Arg Leu Gln Glu Ser Leu
 15              20                  25                      30

CAG CAG AGA GCA CTG CGC ACG CGC CTG CGC CTG CAG ACC ATG ACC CTC         146
Gln Gln Arg Ala Leu Arg Thr Arg Leu Arg Leu Gln Thr Met Thr Leu
             35                  40                  45

GAG CAC GTG CTG CGC TTC CTG CGC CGA AAC GCC TTC ATT CTG CTG ACG         194
Glu His Val Leu Arg Phe Leu Arg Arg Asn Ala Phe Ile Leu Leu Thr
                 50                  55                  60

GTC AGC GCC GTG GTC ATT GGG GTC AGC CTG GCC TTT GCC CTG CGC CCA         242
Val Ser Ala Val Val Ile Gly Val Ser Leu Ala Phe Ala Leu Arg Pro
             65                  70                  75

TAT CAG CTC ACC TAC CGC CAG ATC AAG TAC TTC TCT TTT CCT GGA GAG         290
Tyr Gln Leu Thr Tyr Arg Gln Ile Lys Tyr Phe Ser Phe Pro Gly Glu
     80                  85                  90

CTT CTG ATG AGG ATG CTG CAG ATG CTG GTG TTA CCT CTC ATT GTC TCC         338
Leu Leu Met Arg Met Leu Gln Met Leu Val Leu Pro Leu Ile Val Ser
 95              100                 105                     110

AGC CTG GTC ACA GGT ATG GCA TCC CTG GAC AAC AAG GCC ACG GGG CGG         386
Ser Leu Val Thr Gly Met Ala Ser Leu Asp Asn Lys Ala Thr Gly Arg
             115                 120                 125

ATG GGG ATG CGG GCA GCT GTG TAC TAC ATG GTG ACC ACC ATC ATC GCG         434
Met Gly Met Arg Ala Ala Val Tyr Tyr Met Val Thr Thr Ile Ile Ala
             130                 135                 140

GTC TTC ATC GGC ATC CTC ATG GTC ACC ATC ATC CAT CCC GGG AAG GGC         482
Val Phe Ile Gly Ile Leu Met Val Thr Ile Ile His Pro Gly Lys Gly
             145                 150                 155

TCC AAG GAG GGG CTG CAC CGG GAG GGC CGG ATC GAG ACC ATC CCC ACA         530
Ser Lys Glu Gly Leu His Arg Glu Gly Arg Ile Glu Thr Ile Pro Thr
 160                 165                 170

GCT GAT GCC TTC ATG GAC CTG ATC AGA AAT ATG TTT CCA CCA AAC CTT         578
Ala Asp Ala Phe Met Asp Leu Ile Arg Asn Met Phe Pro Pro Asn Leu
 175                 180                 185                 190

GTG GAG GCC TGC TTC AAA CAG TTC AAG ACG CAG TAC AGC ACG AGG GTG         626
Val Glu Ala Cys Phe Lys Gln Phe Lys Thr Gln Tyr Ser Thr Arg Val
             195                 200                 205

GTA ACC AGG ACC ATG GTG AGG ACA GAG AAC GGG TCT GAG CCG GGT GCC         674
Val Thr Arg Thr Met Val Arg Thr Glu Asn Gly Ser Glu Pro Gly Ala
             210                 215                 220

TCC ATG CCT CCT CCA TTC TCA GTG GAG AAC GGA ACC AGC TTC CTG GAA         722
Ser Met Pro Pro Pro Phe Ser Val Glu Asn Gly Thr Ser Phe Leu Glu
 225                 230                 235

AAT GTC ACT CGG GCC TTG GGT ACC CTG CAG GAG ATG CTG AGC TTT GAG         770
Asn Val Thr Arg Ala Leu Gly Thr Leu Gln Glu Met Leu Ser Phe Glu
 240                 245                 250

GAG ACT GTA CCC GTG CCT GGC TCC GCC AAT GGC ATC AAC GCC CTG GGC         818
Glu Thr Val Pro Val Pro Gly Ser Ala Asn Gly Ile Asn Ala Leu Gly
 255                 260                 265                 270

CTC GTG GTC TTC TCT GTG GCC TTT GGG CTG GTC ATT GGT GGC ATG AAA         866
Leu Val Val Phe Ser Val Ala Phe Gly Leu Val Ile Gly Gly Met Lys
             275                 280                 285

CAC AAG GGC AGA GTC CTC AGG GAC TTC TTC GAC AGC CTC AAT GAG GCT         914
His Lys Gly Arg Val Leu Arg Asp Phe Phe Asp Ser Leu Asn Glu Ala
             290                 295                 300

ATT ATG AGG CTG GTG GGC ATC ATT ATC TGG TAT GCA CCT GTG GGC ATC         962
Ile Met Arg Leu Val Gly Ile Ile Ile Trp Tyr Ala Pro Val Gly Ile
             305                 310                 315
```

```
CTG TTC CTG ATT GCT GGG AAG ATT CTG GAG ATG GAA GAC ATG GCC GTC      1010
Leu Phe Leu Ile Ala Gly Lys Ile Leu Glu Met Glu Asp Met Ala Val
    320                 325                 330

CTG GGG GGT CAG CTG GGC ATG TAC ACC CTG ACC GTC ATC GTG GGC CTG      1058
Leu Gly Gly Gln Leu Gly Met Tyr Thr Leu Thr Val Ile Val Gly Leu
335                 340                 345                 350

TTC CTC CAT GCC GGC ATT GTC CTT CCC CTC ATC TAC TTC CTC GTC ACT      1106
Phe Leu His Ala Gly Ile Val Leu Pro Leu Ile Tyr Phe Leu Val Thr
                355                 360                 365

CAC CGG AAC CCC TTC CCC TTC ATT GGG GGC ATG CTA CAA GCC CTC ATC      1154
His Arg Asn Pro Phe Pro Phe Ile Gly Gly Met Leu Gln Ala Leu Ile
            370                 375                 380

ACC GCT ATG GGC ACG TCT TCC AGC TCG GCA ACG CTG CCC ATC ACC TTC      1202
Thr Ala Met Gly Thr Ser Ser Ser Ser Ala Thr Leu Pro Ile Thr Phe
        385                 390                 395

CGC TGC CTG GAG GAG GGC CTG GGT GTG GAC CGC CGC ATC ACC AGG TTC      1250
Arg Cys Leu Glu Glu Gly Leu Gly Val Asp Arg Arg Ile Thr Arg Phe
    400                 405                 410

GTC CTG CCC GTG GGC GCC ACG GTC AAC ATG GAT GGC ACT GCC CTC TAC      1298
Val Leu Pro Val Gly Ala Thr Val Asn Met Asp Gly Thr Ala Leu Tyr
415                 420                 425                 430

GAG GCC CTG GCT GCC ATC TTC ATT GCT CAA GTT AAC AAC TAC GAG CTC      1346
Glu Ala Leu Ala Ala Ile Phe Ile Ala Gln Val Asn Asn Tyr Glu Leu
                435                 440                 445

AAC CTG GGT CAG ATC ACA ACC ATC AGC ATC ACG GCC ACA GCA GCC AGT      1394
Asn Leu Gly Gln Ile Thr Thr Ile Ser Ile Thr Ala Thr Ala Ala Ser
            450                 455                 460

GTT GGG GCT GCT GGC ATC CCC CAG GCG GGT CTG GTC ACC ATG GTC ATT      1442
Val Gly Ala Ala Gly Ile Pro Gln Ala Gly Leu Val Thr Met Val Ile
        465                 470                 475

GTG CTT ACG TCG GTC GGC TTG CCC ACG GAA GAC ATC ACG CTC ATC ATC      1490
Val Leu Thr Ser Val Gly Leu Pro Thr Glu Asp Ile Thr Leu Ile Ile
    480                 485                 490

GCC GTG GAC TGG TTC CTT GAC CGG CTT CGC ACA ATG ACC AAC GTA CTG      1538
Ala Val Asp Trp Phe Leu Asp Arg Leu Arg Thr Met Thr Asn Val Leu
495                 500                 505                 510

GGC CAC TCA ATT GGA GCG GCC GTC ATC GAG CAC TTG TCT CAG CGG GAG      1586
Gly His Ser Ile Gly Ala Ala Val Ile Glu His Leu Ser Gln Arg Glu
                515                 520                 525

CTG GAG CTT CAG GAA GCT GAG CTT ACC CTC CCC AGC CTG GGG AAA CCC      1634
Leu Glu Leu Gln Glu Ala Glu Leu Thr Leu Pro Ser Leu Gly Lys Pro
            530                 535                 540

TAC AAG TCC CTC ATG GCA CAG GAG AAG GGG GCA TCC CGG GGA CGG GGA      1682
Tyr Lys Ser Leu Met Ala Gln Glu Lys Gly Ala Ser Arg Gly Arg Gly
        545                 550                 555

GGC AAC GAG AGT GCT ATG TGAGGGGCCT CCAGCTCTGC CCCCCAGAG AGGA         1734
Gly Asn Glu Ser Ala Met
560                 565
```

(2) INFORMATION FOR SEQ ID NO:2:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Ser His Gly Asn Ser Leu Phe Leu Arg Glu Ser Gly Gln Arg
1               5                   10                  15
```

```
Leu Gly Arg Val Gly Trp Leu Gln Arg Leu Gln Glu Ser Leu Gln Gln
            20                  25                  30

Arg Ala Leu Arg Thr Arg Leu Arg Leu Gln Thr Met Thr Leu Glu His
        35                  40                  45

Val Leu Arg Phe Leu Arg Arg Asn Ala Phe Ile Leu Leu Thr Val Ser
    50                  55                  60

Ala Val Val Ile Gly Val Ser Leu Ala Phe Ala Leu Arg Pro Tyr Gln
65                  70                  75                  80

Leu Thr Tyr Arg Gln Ile Lys Tyr Phe Ser Phe Pro Gly Glu Leu Leu
                85                  90                  95

Met Arg Met Leu Gln Met Leu Val Leu Pro Leu Ile Val Ser Ser Leu
            100                 105                 110

Val Thr Gly Met Ala Ser Leu Asp Asn Lys Ala Thr Gly Arg Met Gly
        115                 120                 125

Met Arg Ala Ala Val Tyr Tyr Met Val Thr Thr Ile Ile Ala Val Phe
    130                 135                 140

Ile Gly Ile Leu Met Val Thr Ile Ile His Pro Gly Lys Gly Ser Lys
145                 150                 155                 160

Glu Gly Leu His Arg Glu Gly Arg Ile Glu Thr Ile Pro Thr Ala Asp
                165                 170                 175

Ala Phe Met Asp Leu Ile Arg Asn Met Phe Pro Pro Asn Leu Val Glu
            180                 185                 190

Ala Cys Phe Lys Gln Phe Lys Thr Gln Tyr Ser Thr Arg Val Val Thr
        195                 200                 205

Arg Thr Met Val Arg Thr Glu Asn Gly Ser Glu Pro Gly Ala Ser Met
    210                 215                 220

Pro Pro Pro Phe Ser Val Glu Asn Gly Thr Ser Phe Leu Glu Asn Val
225                 230                 235                 240

Thr Arg Ala Leu Gly Thr Leu Gln Glu Met Leu Ser Phe Glu Glu Thr
                245                 250                 255

Val Pro Val Pro Gly Ser Ala Asn Gly Ile Asn Ala Leu Gly Leu Val
            260                 265                 270

Val Phe Ser Val Ala Phe Gly Leu Val Ile Gly Gly Met Lys His Lys
        275                 280                 285

Gly Arg Val Leu Arg Asp Phe Phe Asp Ser Leu Asn Glu Ala Ile Met
    290                 295                 300

Arg Leu Val Gly Ile Ile Ile Trp Tyr Ala Pro Val Gly Ile Leu Phe
305                 310                 315                 320

Leu Ile Ala Gly Lys Ile Leu Glu Met Glu Asp Met Ala Val Leu Gly
                325                 330                 335

Gly Gln Leu Gly Met Tyr Thr Leu Thr Val Ile Val Gly Leu Phe Leu
            340                 345                 350

His Ala Gly Ile Val Leu Pro Leu Ile Tyr Phe Leu Val Thr His Arg
        355                 360                 365

Asn Pro Phe Pro Phe Ile Gly Gly Met Leu Gln Ala Leu Ile Thr Ala
    370                 375                 380

Met Gly Thr Ser Ser Ser Ser Ala Thr Leu Pro Ile Thr Phe Arg Cys
385                 390                 395                 400

Leu Glu Glu Gly Leu Gly Val Asp Arg Arg Ile Thr Arg Phe Val Leu
                405                 410                 415

Pro Val Gly Ala Thr Val Asn Met Asp Gly Thr Ala Leu Tyr Glu Ala
            420                 425                 430

Leu Ala Ala Ile Phe Ile Ala Gln Val Asn Asn Tyr Glu Leu Asn Leu
```

```
                    435                 440                 445
Gly Gln Ile Thr Thr Ile Ser Ile Thr Ala Thr Ala Ala Ser Val Gly
                450                 455                 460

Ala Ala Gly Ile Pro Gln Ala Gly Leu Val Thr Met Val Ile Val Leu
465                 470                 475                 480

Thr Ser Val Gly Leu Pro Thr Glu Asp Ile Thr Leu Ile Ile Ala Val
                485                 490                 495

Asp Trp Phe Leu Asp Arg Leu Arg Thr Met Thr Asn Val Leu Gly His
                500                 505                 510

Ser Ile Gly Ala Ala Val Ile Glu His Leu Ser Gln Arg Glu Leu Glu
                515                 520                 525

Leu Gln Glu Ala Glu Leu Thr Leu Pro Ser Leu Gly Lys Pro Tyr Lys
                530                 535                 540

Ser Leu Met Ala Gln Glu Lys Gly Ala Ser Arg Gly Arg Gly Gly Asn
545                 550                 555                 560

Glu Ser Ala Met (2) INFORMATION FOR SEQ ID NO:3:

(i) SEQUENCE CHARACTERISTICS:
        (A) LENGTH: 1680 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..30

(ix) FEATURE:
        (A) NAME/KEY: CDS
        (B) LOCATION: 31..1656

(ix) FEATURE:
        (A) NAME/KEY: 3'UTR
        (B) LOCATION: 1657..1680

(xi) SEQUENCE DESCRIPTION: SEQ ID NO:3:

AAAGAAGAGA CCCTCCTAGA AAAGTAAAAT ATG ACT AAA AGC AAT GGA GAA GAG       54
                                Met Thr Lys Ser Asn Gly Glu Glu
                                  1               5

CCC AAG ATG GGG GGC AGG ATG GAG AGA TTC CAG CAG GGA GTC CGT AAA      102
Pro Lys Met Gly Gly Arg Met Glu Arg Phe Gln Gln Gly Val Arg Lys
 10                  15                  20

CGC ACA CTT TTG GCC AAG AAG AAA GTG CAG AAC ATT ACA AAG GAG GTT      150
Arg Thr Leu Leu Ala Lys Lys Lys Val Gln Asn Ile Thr Lys Glu Val
 25                  30                  35                  40

GTT AAA AGT TAC CTG TTT CGG AAT GCT TTT GTG CTG CTC ACA GTC ACC      198
Val Lys Ser Tyr Leu Phe Arg Asn Ala Phe Val Leu Leu Thr Val Thr
                 45                  50                  55

GCT GTC ATT GTG GGT ACA ATC CTT GGA TTT ACC CTC CGA CCA TAC AGA      246
Ala Val Ile Val Gly Thr Ile Leu Gly Phe Thr Leu Arg Pro Tyr Arg
                 60                  65                  70

ATG AGC TAC CGG GAA GTC AAG TAC TTC TCC TTT CCT GGG GAA CTT CTG      294
Met Ser Tyr Arg Glu Val Lys Tyr Phe Ser Phe Pro Gly Glu Leu Leu
 75                  80                  85

ATG AGG ATG TTA CAG ATG CTG GTC TTA CCA CTT ATC ATC TCC AGT CTT      342
Met Arg Met Leu Gln Met Leu Val Leu Pro Leu Ile Ile Ser Ser Leu
 90                  95                 100

GTC ACA GGA ATG GCG GCG CTA GAT AGT AAG GCA TCA GGG AAG TGG GAA      390
```

```
Val Thr Gly Met Ala Ala Leu Asp Ser Lys Ala Ser Gly Lys Trp Glu
105                 110                 115                 120

TGC GGA GCT GTA GTC TAT TAT ATG ACT ACC ACC ATC ATT GCT GTG GTG         438
Cys Gly Ala Val Val Tyr Tyr Met Thr Thr Thr Ile Ile Ala Val Val
                125                 130                 135

ATT GGC ATA ATC ATT GTC ATC ATC ATC CAT CCT GGG AAG GGC ACA AAG         486
Ile Gly Ile Ile Ile Val Ile Ile Ile His Pro Gly Lys Gly Thr Lys
            140                 145                 150

GAA AAC ATG CAC AGA GAA GGC AAA ATT GTA CGA GTG ACA GCT GCA GAT         534
Glu Asn Met His Arg Glu Gly Lys Ile Val Arg Val Thr Ala Ala Asp
            155                 160                 165

GCC TTC CTG GAC TTG ATC AGG AAC ATG TTA AAT CCA AAT CTG GTA GAA         582
Ala Phe Leu Asp Leu Ile Arg Asn Met Leu Asn Pro Asn Leu Val Glu
170                 175                 180

GCC TGC TTT AAA CAG TTT AAA ACC AAC TAT GAG AAG AGA AGC TTT AAA         630
Ala Cys Phe Lys Gln Phe Lys Thr Asn Tyr Glu Lys Arg Ser Phe Lys
185                 190                 195                 200

GTG CCC ATC CAG GCC AAC GAA ACG CTT GTG GGT GCT GTG ATA AAC AAT         678
Val Pro Ile Gln Ala Asn Glu Thr Leu Val Gly Ala Val Ile Asn Asn
                205                 210                 215

GTG TCT GAG GCC ATG GAG ACT CTT ACC CGA ATC ACA GAG GAG CTG GTC         726
Val Ser Glu Ala Met Glu Thr Leu Thr Arg Ile Thr Glu Glu Leu Val
            220                 225                 230

CCA GTT CCA GGA TCT GTG AAT GGA GTC AAT GCC CTG GGT CTA GTT GTC         774
Pro Val Pro Gly Ser Val Asn Gly Val Asn Ala Leu Gly Leu Val Val
            235                 240                 245

TTC TCC ATG TGC TTC GGT TTT GTG ATT GGA AAC ATG AAG GAA CAG GGG         822
Phe Ser Met Cys Phe Gly Phe Val Ile Gly Asn Met Lys Glu Gln Gly
            250                 255                 260

CAG GCC CTG AGA GAG TTC TTT GAT TCT CTT AAC GAA GCC ATC ATG AGA         870
Gln Ala Leu Arg Glu Phe Phe Asp Ser Leu Asn Glu Ala Ile Met Arg
265                 270                 275                 280

CTG GTA GCA GTA ATA ATG TGG TAT GCC CCC GTG GGT ATT CTC TTC CTG         918
Leu Val Ala Val Ile Met Trp Tyr Ala Pro Val Gly Ile Leu Phe Leu
                285                 290                 295

ATT GCT GGG AAG ATT GTG GAG ATG GAA GAC ATG GGT GTG ATT GGG GGG         966
Ile Ala Gly Lys Ile Val Glu Met Glu Asp Met Gly Val Ile Gly Gly
            300                 305                 310

CAG CTT GCC ATG TAC ACC GTG ACT GTC ATT GTT GGC TTA CTC ATT CAC        1014
Gln Leu Ala Met Tyr Thr Val Thr Val Ile Val Gly Leu Leu Ile His
            315                 320                 325

GCA GTC ATC GTC TTG CCA CTC CTC TAC TTC TTG GTA ACA CGG AAA AAC        1062
Ala Val Ile Val Leu Pro Leu Leu Tyr Phe Leu Val Thr Arg Lys Asn
330                 335                 340

CCT TGG GTT TTT ATT GGA GGG TTG CTG CAA GCA CTC ATC ACC GCT CTG        1110
Pro Trp Val Phe Ile Gly Gly Leu Leu Gln Ala Leu Ile Thr Ala Leu
345                 350                 355                 360

GGG ACC TCT TCA AGT TCT GCC ACC CTA CCC ATC ACC TTC AAG TGC CTG        1158
Gly Thr Ser Ser Ser Ser Ala Thr Leu Pro Ile Thr Phe Lys Cys Leu
                365                 370                 375

GAA GAG AAC AAT GGC GTG GAC AAG CGC GTC ACC AGA TTC GTG CTC CCC        1206
Glu Glu Asn Asn Gly Val Asp Lys Arg Val Thr Arg Phe Val Leu Pro
            380                 385                 390

GTA GGA GCC ACC ATT AAC ATG GAT GGG ACT GCC CTC TAT GAG GCT TTG        1254
Val Gly Ala Thr Ile Asn Met Asp Gly Thr Ala Leu Tyr Glu Ala Leu
            395                 400                 405

GCT GCC ATT TTC ATT GCT CAA GTT AAC AAC TTT GAA CTG AAC TTC GGA        1302
Ala Ala Ile Phe Ile Ala Gln Val Asn Asn Phe Glu Leu Asn Phe Gly
410                 415                 420
```

```
CAA ATT ATT ACA ATC AGC ATC ACA GCC ACA GCT GCC AGT ATT GGG GCA          1350
Gln Ile Ile Thr Ile Ser Ile Thr Ala Thr Ala Ala Ser Ile Gly Ala
425                 430                 435                 440

GCT GGA ATT CCT CAG GCG GGC CTG GTC ACT ATG GTC ATT GTG CTG ACA          1398
Ala Gly Ile Pro Gln Ala Gly Leu Val Thr Met Val Ile Val Leu Thr
                445                 450                 455

TCT GTC GGC CTG CCC ACT GAC GAC ATC ACG CTC ATC ATC GCG GTG GAC          1446
Ser Val Gly Leu Pro Thr Asp Asp Ile Thr Leu Ile Ile Ala Val Asp
            460                 465                 470

TGG TTC TTG GAT CGC CTC CGG ACC ACC ACC AAC GTA CTG GGA GAC TCC          1494
Trp Phe Leu Asp Arg Leu Arg Thr Thr Thr Asn Val Leu Gly Asp Ser
        475                 480                 485

CTG GGA GCT GGG ATT GTG GAG CAC TTG TCA CGA CAT GAA CTG AAG AAC          1542
Leu Gly Ala Gly Ile Val Glu His Leu Ser Arg His Glu Leu Lys Asn
    490                 495                 500

AGA GAT GTT GAA ATG GGT AAC TCA GTG ATT GAA GAG AAT GAA ATG AAG          1590
Arg Asp Val Glu Met Gly Asn Ser Val Ile Glu Glu Asn Glu Met Lys
505                 510                 515                 520

AAA CCA TAT CAA CTG ATT GCA CAG GAC AAT GAA ACT GAG AAA CCC ATC          1638
Lys Pro Tyr Gln Leu Ile Ala Gln Asp Asn Glu Thr Glu Lys Pro Ile
                525                 530                 535

GAC AGT GAA ACC AAG ATG TAGACTAACA TAAAGAAACA CTTT                       1680
Asp Ser Glu Thr Lys Met
            540

(2) INFORMATION FOR SEQ ID NO:4:

(i) SEQUENCE CHARACTERISTICS:
        (A) LENGTH: 542 amino acids
        (B) TYPE: amino acid
        (D) TOPOLOGY: linear (ii) MOLECULE TYPE: protein (xi) SEQUENCE DESCRIPTION: SEQ ID NO:4:

Met Thr Lys Ser Asn Gly Glu Glu Pro Lys Met Gly Gly Arg Met Glu
 1               5                  10                  15

Arg Phe Gln Gln Gly Val Arg Lys Arg Thr Leu Leu Ala Lys Lys Lys
            20                  25                  30

Val Gln Asn Ile Thr Lys Glu Val Val Lys Ser Tyr Leu Phe Arg Asn
        35                  40                  45

Ala Phe Val Leu Leu Thr Val Thr Ala Val Ile Val Gly Thr Ile Leu
    50                  55                  60

Gly Phe Thr Leu Arg Pro Tyr Arg Met Ser Tyr Arg Glu Val Lys Tyr
65                  70                  75                  80

Phe Ser Phe Pro Gly Glu Leu Leu Met Arg Met Leu Gln Met Leu Val
            85                  90                  95

Leu Pro Leu Ile Ile Ser Ser Leu Val Thr Gly Met Ala Ala Leu Asp
            100                 105                 110

Ser Lys Ala Ser Gly Lys Trp Glu Cys Gly Ala Val Tyr Tyr Met
        115                 120                 125

Thr Thr Thr Ile Ile Ala Val Val Gly Ile Ile Ile Val Ile Ile
    130                 135                 140

Ile His Pro Gly Lys Gly Thr Lys Glu Asn Met His Arg Glu Gly Lys
145                 150                 155                 160

Ile Val Arg Val Thr Ala Ala Asp Ala Phe Leu Asp Leu Ile Arg Asn
            165                 170                 175

Met Leu Asn Pro Asn Leu Val Glu Ala Cys Phe Lys Gln Phe Lys Thr
        180                 185                 190
```

```
Asn Tyr Glu Lys Arg Ser Phe Lys Val Pro Ile Gln Ala Asn Glu Thr
            195                 200                 205

Leu Val Gly Ala Val Ile Asn Asn Val Ser Glu Ala Met Glu Thr Leu
            210                 215                 220

Thr Arg Ile Thr Glu Glu Leu Val Pro Val Pro Gly Ser Val Asn Gly
225                 230                 235                 240

Val Asn Ala Leu Gly Leu Val Val Phe Ser Met Cys Phe Gly Phe Val
                245                 250                 255

Ile Gly Asn Met Lys Glu Gln Gly Gln Ala Leu Arg Glu Phe Phe Asp
                260                 265                 270

Ser Leu Asn Glu Ala Ile Met Arg Leu Val Ala Val Ile Met Trp Tyr
            275                 280                 285

Ala Pro Val Gly Ile Leu Phe Leu Ile Ala Gly Lys Ile Val Glu Met
            290                 295                 300

Glu Asp Met Gly Val Ile Gly Gly Gln Leu Ala Met Tyr Thr Val Thr
305                 310                 315                 320

Val Ile Val Gly Leu Leu Ile His Ala Val Ile Val Leu Pro Leu Leu
                325                 330                 335

Tyr Phe Leu Val Thr Arg Lys Asn Pro Trp Val Phe Ile Gly Gly Leu
                340                 345                 350

Leu Gln Ala Leu Ile Thr Ala Leu Gly Thr Ser Ser Ser Ser Ala Thr
            355                 360                 365

Leu Pro Ile Thr Phe Lys Cys Leu Glu Glu Asn Asn Gly Val Asp Lys
            370                 375                 380

Arg Val Thr Arg Phe Val Leu Pro Val Gly Ala Thr Ile Asn Met Asp
385                 390                 395                 400

Gly Thr Ala Leu Tyr Glu Ala Leu Ala Ala Ile Phe Ile Ala Gln Val
                405                 410                 415

Asn Asn Phe Glu Leu Asn Phe Gly Gln Ile Ile Thr Ile Ser Ile Thr
                420                 425                 430

Ala Thr Ala Ala Ser Ile Gly Ala Ala Gly Ile Pro Gln Ala Gly Leu
            435                 440                 445

Val Thr Met Val Ile Val Leu Thr Ser Val Gly Leu Pro Thr Asp Asp
            450                 455                 460

Ile Thr Leu Ile Ile Ala Val Asp Trp Phe Leu Asp Arg Leu Arg Thr
465                 470                 475                 480

Thr Thr Asn Val Leu Gly Asp Ser Leu Gly Ala Gly Ile Val Glu His
                485                 490                 495

Leu Ser Arg His Glu Leu Lys Asn Arg Asp Val Glu Met Gly Asn Ser
            500                 505                 510

Val Ile Glu Glu Asn Glu Met Lys Lys Pro Tyr Gln Leu Ile Ala Gln
            515                 520                 525

Asp Asn Glu Thr Glu Lys Pro Ile Asp Ser Glu Thr Lys Met
530                 535                 540
```

(2) INFORMATION FOR SEQ ID NO:5:

(i) SEQUENCE CHARACTERISTICS:
        (A) LENGTH: 1800 base pairs
        (B) TYPE: nucleic acid
        (C) STRANDEDNESS: single
        (D) TOPOLOGY: linear (ii) MOLECULE TYPE: cDNA (ix) FEATURE:

```
            (A) NAME/KEY: 5'UTR
            (B) LOCATION: 1..33

(ix) FEATURE:
            (A) NAME/KEY: CDS
            (B) LOCATION: 34..1755

(ix) FEATURE:
            (A) NAME/KEY: 3'UTR
            (B) LOCATION: 1756..1800

(xi) SEQUENCE DESCRIPTION: SEQ ID NO:5:

GATAGTGCTG AAGAGGAGGG GCGTTCCCAG ACC ATG GCA TCT ACG GAA GGT GCC        54
                                    Met Ala Ser Thr Glu Gly Ala
                                      1               5

AAC AAT ATG CCC AAG CAG GTG GAA GTG CGA ATG CCA GAC AGT CAT CTT       102
Asn Asn Met Pro Lys Gln Val Glu Val Arg Met Pro Asp Ser His Leu
         10                  15                  20

GGC TCA GAG GAA CCC AAG CAC CGG CAC CTG GGC CTG CGC CTG TGT GAC       150
Gly Ser Glu Glu Pro Lys His Arg His Leu Gly Leu Arg Leu Cys Asp
     25                  30                  35

AAG CTG GGG AAG AAT CTG CTG CTC ACC CTG ACG GTG TTT GGT GTC ATC       198
Lys Leu Gly Lys Asn Leu Leu Leu Thr Leu Thr Val Phe Gly Val Ile
 40                  45                  50                  55

CTG GGA GCA GTG TGT GGA GGG CTT CTT CGC TTG GCA TCT CCC ATC CAC       246
Leu Gly Ala Val Cys Gly Gly Leu Leu Arg Leu Ala Ser Pro Ile His
                 60                  65                  70

CCT GAT GTG GTT ATG TTA ATA GCC TTC CCA GGG GAT ATA CTC ATG AGG       294
Pro Asp Val Val Met Leu Ile Ala Phe Pro Gly Asp Ile Leu Met Arg
             75                  80                  85

ATG CTA AAA ATG CTC ATT CTG GGT CTA ATC ATC TCC AGC TTA ATC ACA       342
Met Leu Lys Met Leu Ile Leu Gly Leu Ile Ile Ser Ser Leu Ile Thr
         90                  95                 100

GGG TTG TCA GGC CTG GAT GCT AAG GCT AGT GGC CGC TTG GGC ACG AGA       390
Gly Leu Ser Gly Leu Asp Ala Lys Ala Ser Gly Arg Leu Gly Thr Arg
    105                 110                 115

GCC ATG GTG TAT TAC ATG TCC ACG ACC ATC ATT GCT GCA GTA CTG GGG       438
Ala Met Val Tyr Tyr Met Ser Thr Thr Ile Ile Ala Ala Val Leu Gly
120                 125                 130                 135

GTC ATT CTG GTC TTG GCT ATC CAT CCA GGC AAT CCC AAG CTC AAG AAG       486
Val Ile Leu Val Leu Ala Ile His Pro Gly Asn Pro Lys Leu Lys Lys
                140                 145                 150

CAG CTG GGG CCT GGG AAG AAG AAT GAT GAA GTG TCC AGC CTG GAT GCC       534
Gln Leu Gly Pro Gly Lys Lys Asn Asp Glu Val Ser Ser Leu Asp Ala
            155                 160                 165

TTC CTG GAC CTT ATT CGA AAT CTC TTC CCT GAA AAC TTG GTC CAA GCC       582
Phe Leu Asp Leu Ile Arg Asn Leu Phe Pro Glu Asn Leu Val Gln Ala
        170                 175                 180

TGC TTT CAA CAG ATT CAA ACA GTG ACG AAG AAA GTC CTG GTT GCA CCA       630
Cys Phe Gln Gln Ile Gln Thr Val Thr Lys Lys Val Leu Val Ala Pro
    185                 190                 195

CCG CCA GAC GAG GAG GCC AAC GCA ACC AGC GCT GAA GTC TCT CTG TTG       678
Pro Pro Asp Glu Glu Ala Asn Ala Thr Ser Ala Glu Val Ser Leu Leu
200                 205                 210                 215

AAC GAG ACT GTG ACT GAG GTG CCG GAG GAG ACT AAG ATG GTT ATC AAG       726
Asn Glu Thr Val Thr Glu Val Pro Glu Glu Thr Lys Met Val Ile Lys
                220                 225                 230

AAG GGC CTG GAG TTC AAG GAT GGG ATG AAC GTC TTA GGT CTG ATA GGG       774
Lys Gly Leu Glu Phe Lys Asp Gly Met Asn Val Leu Gly Leu Ile Gly
            235                 240                 245

TTT TTC ATT GCT TTT GGC ATC GCT ATG GGG AAG ATG GGA GAT CAG GCC       822
Phe Phe Ile Ala Phe Gly Ile Ala Met Gly Lys Met Gly Asp Gln Ala
```

```
                    250                     255                     260
AAG CTG ATG GTG GAT TTC TTC AAC ATT TTG AAT GAG ATT GTA ATG AAG          870
Lys Leu Met Val Asp Phe Phe Asn Ile Leu Asn Glu Ile Val Met Lys
265                     270                     275

TTA GTG ATC ATG ATC ATG TGG TAC TCT CCC CTG GGT ATC GCC TGC CTG          918
Leu Val Ile Met Ile Met Trp Tyr Ser Pro Leu Gly Ile Ala Cys Leu
280                     285                     290                 295

ATC TGT GGA AAG ATC ATT GCA ATC AAG GAC TTA GAA GTG GTT GCT AGG          966
Ile Cys Gly Lys Ile Ile Ala Ile Lys Asp Leu Glu Val Val Ala Arg
                300                     305                     310

CAA CTG GGG ATG TAC ATG GTA ACA GTG ATC ATA GGC CTC ATC ATC CAC         1014
Gln Leu Gly Met Tyr Met Val Thr Val Ile Ile Gly Leu Ile Ile His
            315                     320                     325

GGG GGC ATC TTT CTC CCC TTG ATT TAC TTT GTA GTG ACC AGG AAA AAC         1062
Gly Gly Ile Phe Leu Pro Leu Ile Tyr Phe Val Val Thr Arg Lys Asn
            330                     335                     340

CCC TTC TCC CTT TTT GCT GGC ATT TTC CAA GCT TGG ATC ACT GCC CTG         1110
Pro Phe Ser Leu Phe Ala Gly Ile Phe Gln Ala Trp Ile Thr Ala Leu
345                     350                     355

GGC ACC GCT TCC AGT GCT GGA ACT TTG CCT GTC ACC TTT CGT TGC CTG         1158
Gly Thr Ala Ser Ser Ala Gly Thr Leu Pro Val Thr Phe Arg Cys Leu
360                     365                     370                 375

GAA GAA AAT CTG GGG ATT GAT AAG CGT GTG ACT AGA TTC GTC CTT CCT         1206
Glu Glu Asn Leu Gly Ile Asp Lys Arg Val Thr Arg Phe Val Leu Pro
                380                     385                     390

GTT GGA GCA ACC ATT AAC ATG GAT GGT ACA GCC CTT TAT GAA GCG GTG         1254
Val Gly Ala Thr Ile Asn Met Asp Gly Thr Ala Leu Tyr Glu Ala Val
            395                     400                     405

GCC GCC ATC TTT ATA GCC CAA ATG AAT GGT GTT GTC CTG GAT GGA GGA         1302
Ala Ala Ile Phe Ile Ala Gln Met Asn Gly Val Val Leu Asp Gly Gly
            410                     415                     420

CAG ATT GTG ACT GTA AGC CTC ACA GCC ACC CTG GCA AGC GTC GGC GCG         1350
Gln Ile Val Thr Val Ser Leu Thr Ala Thr Leu Ala Ser Val Gly Ala
    425                     430                     435

GCC AGT ATC CCC AGT GCC GGG CTG GTC ACC ATG CTC CTC ATT CTG ACA         1398
Ala Ser Ile Pro Ser Ala Gly Leu Val Thr Met Leu Leu Ile Leu Thr
440                     445                     450                 455

GCC GTG GGC CTG CCA ACA GAG GAC ATC AGC TTG CTG GTG GCT GTG GAC         1446
Ala Val Gly Leu Pro Thr Glu Asp Ile Ser Leu Leu Val Ala Val Asp
                460                     465                     470

TGG CTG CTG GAC AGG ATG AGA ACT TCA GTC AAT GTT GTG GGT GAC TCT         1494
Trp Leu Leu Asp Arg Met Arg Thr Ser Val Asn Val Val Gly Asp Ser
            475                     480                     485

TTT GGG GCT GGG ATA GTC TAT CAC CTC TCC AAG TCT GAG CTG GAT ACC         1542
Phe Gly Ala Gly Ile Val Tyr His Leu Ser Lys Ser Glu Leu Asp Thr
            490                     495                     500

ATT GAC TCC CAG CAT CGA GTG CAT GAA GAT ATT GAA ATG ACC AAG ACT         1590
Ile Asp Ser Gln His Arg Val His Glu Asp Ile Glu Met Thr Lys Thr
            505                     510                     515

CAA TCC ATT TAT GAT GAC ATG AAG AAC CAC AGG GAA AGC AAC TCT AAT         1638
Gln Ser Ile Tyr Asp Asp Met Lys Asn His Arg Glu Ser Asn Ser Asn
520                     525                     530                 535

CAA TGT GTC TAT GCT GCA CAC AAC TCT GTC ATA GTA GAT GAA TGC AAG         1686
Gln Cys Val Tyr Ala Ala His Asn Ser Val Ile Val Asp Glu Cys Lys
                540                     545                     550

GTA ACT CTG GCA GCC AAT GGA AAG TCA GCC GAC TGC AGT GTT GAG GAA         1734
Val Thr Leu Ala Ala Asn Gly Lys Ser Ala Asp Cys Ser Val Glu Glu
            555                     560                     565

GAA CCT TGG AAA CGT GAG AAA TAAGGATATG AGTCTCAGCA AATTCTTGAA            1785
Glu Pro Trp Lys Arg Glu Lys
```

```
Glu Pro Trp Lys Arg Glu Lys
        570

TAAACTCCCC AGCGT                                                    1800

(2) INFORMATION FOR SEQ ID NO:6:

(i) SEQUENCE CHARACTERISTICS:
        (A) LENGTH: 574 amino acids
        (B) TYPE: amino acid
        (D) TOPOLOGY: linear (ii) MOLECULE TYPE: protein (xi) SEQUENCE DESCRIPTION: SEQ ID NO:6:

Met Ala Ser Thr Glu Gly Ala Asn Asn Met Pro Lys Gln Val Glu Val
 1               5                  10                  15

Arg Met Pro Asp Ser His Leu Gly Ser Glu Pro Lys His Arg His
            20                  25                  30

Leu Gly Leu Arg Leu Cys Asp Lys Leu Gly Lys Asn Leu Leu Leu Thr
            35                  40                  45

Leu Thr Val Phe Gly Val Ile Leu Gly Ala Val Cys Gly Leu Leu
    50                  55                  60

Arg Leu Ala Ser Pro Ile His Pro Asp Val Val Met Leu Ile Ala Phe
65                  70                  75                  80

Pro Gly Asp Ile Leu Met Arg Met Leu Lys Met Leu Ile Leu Gly Leu
                85                  90                  95

Ile Ile Ser Ser Leu Ile Thr Gly Leu Ser Gly Leu Asp Ala Lys Ala
                100                 105                 110

Ser Gly Arg Leu Gly Thr Arg Ala Met Val Tyr Tyr Met Ser Thr Thr
            115                 120                 125

Ile Ile Ala Ala Val Leu Gly Val Ile Leu Val Leu Ala Ile His Pro
    130                 135                 140

Gly Asn Pro Lys Leu Lys Lys Gln Leu Gly Pro Gly Lys Lys Asn Asp
145                 150                 155                 160

Glu Val Ser Ser Leu Asp Ala Phe Leu Asp Leu Ile Arg Asn Leu Phe
                165                 170                 175

Pro Glu Asn Leu Val Gln Ala Cys Phe Gln Gln Ile Gln Thr Val Thr
                180                 185                 190

Lys Lys Val Leu Val Ala Pro Pro Asp Glu Glu Ala Asn Ala Thr
            195                 200                 205

Ser Ala Glu Val Ser Leu Leu Asn Glu Thr Val Thr Glu Val Pro Glu
    210                 215                 220

Glu Thr Lys Met Val Ile Lys Lys Gly Leu Glu Phe Lys Asp Gly Met
225                 230                 235                 240

Asn Val Leu Gly Leu Ile Gly Phe Phe Ile Ala Phe Gly Ile Ala Met
                245                 250                 255

Gly Lys Met Gly Asp Gln Ala Lys Leu Met Val Asp Phe Phe Asn Ile
            260                 265                 270

Leu Asn Glu Ile Val Met Lys Leu Val Ile Met Ile Met Trp Tyr Ser
            275                 280                 285

Pro Leu Gly Ile Ala Cys Leu Ile Cys Gly Lys Ile Ile Ala Ile Lys
    290                 295                 300

Asp Leu Glu Val Val Ala Arg Gln Leu Gly Met Tyr Met Val Thr Val
305                 310                 315                 320

Ile Ile Gly Leu Ile Ile His Gly Gly Ile Phe Leu Pro Leu Ile Tyr
                325                 330                 335
```

```
Phe Val Val Thr Arg Lys Asn Pro Phe Ser Leu Phe Ala Gly Ile Phe
            340                 345                 350

Gln Ala Trp Ile Thr Ala Leu Gly Thr Ala Ser Ser Ala Gly Thr Leu
            355                 360                 365

Pro Val Thr Phe Arg Cys Leu Glu Glu Asn Leu Gly Ile Asp Lys Arg
            370                 375                 380

Val Thr Arg Phe Val Leu Pro Val Gly Ala Thr Ile Asn Met Asp Gly
385                 390                 395                 400

Thr Ala Leu Tyr Glu Ala Val Ala Ala Ile Phe Ile Ala Gln Met Asn
                405                 410                 415

Gly Val Val Leu Asp Gly Gly Gln Ile Val Thr Val Ser Leu Thr Ala
            420                 425                 430

Thr Leu Ala Ser Val Gly Ala Ala Ser Ile Pro Ser Ala Gly Leu Val
            435                 440                 445

Thr Met Leu Leu Ile Leu Thr Ala Val Gly Leu Pro Thr Glu Asp Ile
            450                 455                 460

Ser Leu Leu Val Ala Val Asp Trp Leu Leu Asp Arg Met Arg Thr Ser
465                 470                 475                 480

Val Asn Val Val Gly Asp Ser Phe Gly Ala Gly Ile Val Tyr His Leu
            485                 490                 495

Ser Lys Ser Glu Leu Asp Thr Ile Asp Ser Gln His Arg Val His Glu
            500                 505                 510

Asp Ile Glu Met Thr Lys Thr Gln Ser Ile Tyr Asp Asp Met Lys Asn
            515                 520                 525

His Arg Glu Ser Asn Ser Asn Gln Cys Val Tyr Ala Ala His Asn Ser
530                 535                 540

Val Ile Val Asp Glu Cys Lys Val Thr Leu Ala Ala Asn Gly Lys Ser
545                 550                 555                 560

Ala Asp Cys Ser Val Glu Glu Glu Pro Trp Lys Arg Glu Lys
            565                 570

(2) INFORMATION FOR SEQ ID NO:7:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..15

(ix) FEATURE:
        (A) NAME/KEY: CDS
        (B) LOCATION: 16..1590

(ix) FEATURE:
        (A) NAME/KEY: 3'UTR
        (B) LOCATION: 1591..1674

(xi) SEQUENCE DESCRIPTION: SEQ ID NO:7:

ATAGCGGCGA CAGCC ATG GGG AAA CCG GCG AGG AAA GGA TGC CCG AGT TGG      51
              Met Gly Lys Pro Ala Arg Lys Gly Cys Pro Ser Trp
                1               5                  10

AAG CGC TTC CTG AAG AAT AAC TGG GTG TTG CTG TCC ACC GTG GCC GCG       99
Lys Arg Phe Leu Lys Asn Asn Trp Val Leu Leu Ser Thr Val Ala Ala
          15                  20                  25
```

```
GTG GTG CTA GGC ATT ACC ACA GGA GTC TTG GTT CGA GAA CAC AGC AAC        147
Val Val Leu Gly Ile Thr Thr Gly Val Leu Val Arg Glu His Ser Asn
    30              35                  40

CTC TCA ACT CTA GAG AAA TTC TAC TTT GCT TTT CCT GGA GAA ATT CTA        195
Leu Ser Thr Leu Glu Lys Phe Tyr Phe Ala Phe Pro Gly Glu Ile Leu
 45              50                  55                  60

ATG CGG ATG CTG AAA CTC ATC ATT TTG CCA TTA ATA TCC AGC ATG            243
Met Arg Met Leu Lys Leu Ile Ile Leu Pro Leu Ile Ile Ser Ser Met
                 65                  70                  75

ATT ACA GGT GTT GCT GCA CTG GAT TCC AAC GTA TCC GGA AAA ATT GGT        291
Ile Thr Gly Val Ala Ala Leu Asp Ser Asn Val Ser Gly Lys Ile Gly
             80                  85                  90

CTG CGC GCT GTC GTG TAT TAT TTC TGT ACC ACT CTC ATT GCT GTT ATT        339
Leu Arg Ala Val Val Tyr Tyr Phe Cys Thr Thr Leu Ile Ala Val Ile
         95                  100                 105

CTA GGT ATT GTG CTG GTG GTG AGC ATC AAG CCT GGT GTC ACC CAG AAA        387
Leu Gly Ile Val Leu Val Val Ser Ile Lys Pro Gly Val Thr Gln Lys
    110                 115                 120

GTG GGT GAA ATT GCG AGG ACA GGC AGC ACC CCT GAA GTC AGT ACG GTG        435
Val Gly Glu Ile Ala Arg Thr Gly Ser Thr Pro Glu Val Ser Thr Val
125                 130                 135                 140

GAT GCC ATG TTA GAT CTC ATC AGG AAT ATG TTC CCT GAG AAT CTT GTC        483
Asp Ala Met Leu Asp Leu Ile Arg Asn Met Phe Pro Glu Asn Leu Val
                145                 150                 155

CAG GCC TGT TTT CAG CAG TAC AAA ACT AAG CGT GAA GAA GTG AAG CCT        531
Gln Ala Cys Phe Gln Gln Tyr Lys Thr Lys Arg Glu Glu Val Lys Pro
            160                 165                 170

CCC AGC GAT CCA GAG ATG AAC ATG ACA GAA GAG TCC TTC ACA GCT GTC        579
Pro Ser Asp Pro Glu Met Asn Met Thr Glu Glu Ser Phe Thr Ala Val
        175                 180                 185

ATG ACA ACT GCA ATT TCC AAG AAC AAA ACA AAG GAA TAC AAA ATT GTT        627
Met Thr Thr Ala Ile Ser Lys Asn Lys Thr Lys Glu Tyr Lys Ile Val
    190                 195                 200

GGC ATG TAT TCA GAT GGC ATA AAC GTC CTG GGC TTG ATT GTC TTT TGC        675
Gly Met Tyr Ser Asp Gly Ile Asn Val Leu Gly Leu Ile Val Phe Cys
205                 210                 215                 220

CTT GTC TTT GGA CTT GTC ATT GGA AAA ATG GGA GAA AAG GGA CAA ATT        723
Leu Val Phe Gly Leu Val Ile Gly Lys Met Gly Glu Lys Gly Gln Ile
                225                 230                 235

CTG GTG GAT TTC TTC AAT GCT TTG AGT GAT GCA ACC ATG AAA ATC GTT        771
Leu Val Asp Phe Phe Asn Ala Leu Ser Asp Ala Thr Met Lys Ile Val
            240                 245                 250

CAG ATC ATC ATG TGT TAT ATG CCA CTA GGT ATT TTG TTC CTG ATT GCT        819
Gln Ile Ile Met Cys Tyr Met Pro Leu Gly Ile Leu Phe Leu Ile Ala
        255                 260                 265

GGG AAG ATC ATA GAA GTT GAA GAC TGG GAA ATA TTC GCG AAG CTG GGC        867
Gly Lys Ile Ile Glu Val Glu Asp Trp Glu Ile Phe Arg Lys Leu Gly
    270                 275                 280

CTT TAC ATG GCC ACA GTC CTG ACT GGG CTT GCA ATC CAC TCC ATT GTA        915
Leu Tyr Met Ala Thr Val Leu Thr Gly Leu Ala Ile His Ser Ile Val
285                 290                 295                 300

ATT CTC CCG CTG ATA TAT TTC ATA GTC GTA CGA AAG AAC CCT TTC CGA        963
Ile Leu Pro Leu Ile Tyr Phe Ile Val Val Arg Lys Asn Pro Phe Arg
                305                 310                 315

TTT GCC ATG GGA ATG GCC CAG GCT CTC CTG ACA GCT CTC ATG ATC TCT       1011
Phe Ala Met Gly Met Ala Gln Ala Leu Leu Thr Ala Leu Met Ile Ser
            320                 325                 330

TCC AGT TCA GCA ACA CTG CCT GTC ACC TTC CGC TGT GCT GAA GAA AAT       1059
Ser Ser Ser Ala Thr Leu Pro Val Thr Phe Arg Cys Ala Glu Glu Asn
        335                 340                 345
```

```
AAC CAG GTG GAC AAG AGG ATC ACT CGA TTC GTG TTA CCC GTT GGT GCA      1107
Asn Gln Val Asp Lys Arg Ile Thr Arg Phe Val Leu Pro Val Gly Ala
    350                 355                 360

ACA ATC AAC ATG GAT GGG ACC GCG CTC TAT GAA GCA GTG GCA GCG GTG      1155
Thr Ile Asn Met Asp Gly Thr Ala Leu Tyr Glu Ala Val Ala Ala Val
365                 370                 375                 380

TTT ATT GCA CAG TTG AAT GAC CTG GAC TTG GGC ATT GGG CAG ATC ATC      1203
Phe Ile Ala Gln Leu Asn Asp Leu Asp Leu Gly Ile Gly Gln Ile Ile
                385                 390                 395

ACC ATC AGT ATC ACG GCC ACA TCT GCC AGC ATC GGA GCT GCT GGC GTG      1251
Thr Ile Ser Ile Thr Ala Thr Ser Ala Ser Ile Gly Ala Ala Gly Val
            400                 405                 410

CCC CAG GCT GGC CTG GTG ACC ATG GTG ATT GTG CTG AGT GCC GTG GGC      1299
Pro Gln Ala Gly Leu Val Thr Met Val Ile Val Leu Ser Ala Val Gly
            415                 420                 425

CTG CCC GCC GAG GAT GTC ACC CTG ATC ATT GCT GTC GAC TGG CTC CTG      1347
Leu Pro Ala Glu Asp Val Thr Leu Ile Ile Ala Val Asp Trp Leu Leu
        430                 435                 440

GAC CGG TTC AGG ACC ATG GTC AAC GTC CTT GGT GAT GCT TTT GGG ACG      1395
Asp Arg Phe Arg Thr Met Val Asn Val Leu Gly Asp Ala Phe Gly Thr
445                 450                 455                 460

GGC ATT GTG GAA AAG CTC TCC AAG AAG GAG CTG GAG CAG ATG GAT GTT      1443
Gly Ile Val Glu Lys Leu Ser Lys Lys Glu Leu Glu Gln Met Asp Val
                465                 470                 475

TCA TCT GAA GTC AAC ATT GTG AAT CCC TTT GCC TTG GAA TCC ACA ATC      1491
Ser Ser Glu Val Asn Ile Val Asn Pro Phe Ala Leu Glu Ser Thr Ile
            480                 485                 490

CTT GAC AAC GAA GAC TCA GAC ACC AAG AAG TCT TAT GTC AAT GGA GGC      1539
Leu Asp Asn Glu Asp Ser Asp Thr Lys Lys Ser Tyr Val Asn Gly Gly
        495                 500                 505

TTT GCA GTA GAC AAG TCT GAC ACC ATC TCA TTC ACC CAG ACC TCA CAG      1587
Phe Ala Val Asp Lys Ser Asp Thr Ile Ser Phe Thr Gln Thr Ser Gln
    510                 515                 520

TTC TAGGGCCCCT GGCTGCAGAT GACTGGAAAC AAGGAAGGAC ATTTCGTGAG           1640
Phe
525

AGTCATCTCA AACACGGCTT AAGGAAAAGA GAAA                                1674

(2) INFORMATION FOR SEQ ID NO:8:

(i) SEQUENCE CHARACTERISTICS:
        (A) LENGTH: 525 amino acids
        (B) TYPE: amino acid
        (D) TOPOLOGY: linear (ii) MOLECULE TYPE: protein (xi) SEQUENCE DESCRIPTION: SEQ ID NO:8:

Met Gly Lys Pro Ala Arg Lys Gly Cys Pro Ser Trp Lys Arg Phe Leu
 1               5                  10                  15

Lys Asn Asn Trp Val Leu Leu Ser Thr Val Ala Ala Val Val Leu Gly
                20                  25                  30

Ile Thr Thr Gly Val Leu Val Arg Glu His Ser Asn Leu Ser Thr Leu
            35                  40                  45

Glu Lys Phe Tyr Phe Ala Phe Pro Gly Glu Ile Leu Met Arg Met Leu
        50                  55                  60

Lys Leu Ile Ile Leu Pro Leu Ile Ile Ser Ser Met Ile Thr Gly Val
65                  70                  75                  80

Ala Ala Leu Asp Ser Asn Val Ser Gly Lys Ile Gly Leu Arg Ala Val
```

-continued

```
                    85                  90                  95
Val Tyr Tyr Phe Cys Thr Thr Leu Ile Ala Val Ile Leu Gly Ile Val
                100                 105                 110

Leu Val Val Ser Ile Lys Pro Gly Val Thr Gln Lys Val Gly Glu Ile
            115                 120                 125

Ala Arg Thr Gly Ser Thr Pro Glu Val Ser Thr Val Asp Ala Met Leu
        130                 135                 140

Asp Leu Ile Arg Asn Met Phe Pro Glu Asn Leu Val Gln Ala Cys Phe
145                 150                 155                 160

Gln Gln Tyr Lys Thr Lys Arg Glu Glu Val Lys Pro Pro Ser Asp Pro
                165                 170                 175

Glu Met Asn Met Thr Glu Glu Ser Phe Thr Ala Val Met Thr Thr Ala
            180                 185                 190

Ile Ser Lys Asn Lys Thr Lys Glu Tyr Lys Ile Val Gly Met Tyr Ser
        195                 200                 205

Asp Gly Ile Asn Val Leu Gly Leu Ile Val Phe Cys Leu Val Phe Gly
    210                 215                 220

Leu Val Ile Gly Lys Met Gly Glu Lys Gly Gln Ile Leu Val Asp Phe
225                 230                 235                 240

Phe Asn Ala Leu Ser Asp Ala Thr Met Lys Ile Val Gln Ile Ile Met
                245                 250                 255

Cys Tyr Met Pro Leu Gly Ile Leu Phe Leu Ile Ala Gly Lys Ile Ile
            260                 265                 270

Glu Val Glu Asp Trp Glu Ile Phe Arg Lys Leu Gly Leu Tyr Met Ala
        275                 280                 285

Thr Val Leu Thr Gly Leu Ala Ile His Ser Ile Val Ile Leu Pro Leu
    290                 295                 300

Ile Tyr Phe Ile Val Val Arg Lys Asn Pro Phe Arg Phe Ala Met Gly
305                 310                 315                 320

Met Ala Gln Ala Leu Leu Thr Ala Leu Met Ile Ser Ser Ser Ser Ala
                325                 330                 335

Thr Leu Pro Val Thr Phe Arg Cys Ala Glu Glu Asn Asn Gln Val Asp
            340                 345                 350

Lys Arg Ile Thr Arg Phe Val Leu Pro Val Gly Ala Thr Ile Asn Met
        355                 360                 365

Asp Gly Thr Ala Leu Tyr Glu Ala Val Ala Ala Val Phe Ile Ala Gln
    370                 375                 380

Leu Asn Asp Leu Asp Leu Gly Ile Gly Gln Ile Ile Thr Ile Ser Ile
385                 390                 395                 400

Thr Ala Thr Ser Ala Ser Ile Gly Ala Ala Gly Val Pro Gln Ala Gly
                405                 410                 415

Leu Val Thr Met Val Ile Val Leu Ser Ala Val Gly Leu Pro Ala Glu
            420                 425                 430

Asp Val Thr Leu Ile Ile Ala Val Asp Trp Leu Leu Asp Arg Phe Arg
        435                 440                 445

Thr Met Val Asn Val Leu Gly Asp Ala Phe Gly Thr Gly Ile Val Glu
    450                 455                 460

Lys Leu Ser Lys Lys Glu Leu Glu Gln Met Asp Val Ser Ser Glu Val
465                 470                 475                 480

Asn Ile Val Asn Pro Phe Ala Leu Glu Ser Thr Ile Leu Asp Asn Glu
                485                 490                 495

Asp Ser Asp Thr Lys Lys Ser Tyr Val Asn Gly Gly Phe Ala Val Asp
            500                 505                 510
```

```
Lys Ser Asp Thr Ile Ser Phe Thr Gln Thr Ser Gln Phe
    515                 520                 525
```

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
CGCGGGTACC AAYCTSGTVS ARGCYTGYTT Y                           31
```

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CGCGTCTAGA YTGDGCDATR AARAYBGCDG C                           31
```

(2) INFORMATION FOR SEQ ID NO:11:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
CTGRGCRATG AARATGGCAG CCAGGGCYTC ATACAGGGCT GTGCCRTCCA       50
TGTTRATGGT RGC                                               63
```

(2) INFORMATION FOR SEQ ID NO:12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

```
GCGCGTCGAC AAGCTTGCCA TGCAACAGCC TGTT                        34
```

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear

```
        (ii) MOLECULE TYPE: cDNA (xi) SEQUENCE DESCRIPTION: SEQ ID NO:13:

GCGCTCTAGA TCAGCCCACG GTCAGTTG                                              28
```

POLYNUCLEOTIDES ENCODING HUMAN EXCITATORY AMINO ACID TRANSPORTER 4 (EAAT4)

This application is a divisional of U.S. Ser. No. 09/332,740, filed Jun. 14, 1999, now U.S. Pat. No. 6,060,307, issued May 9, 2000, which is a divisional of U.S. Ser. No. 08/663,808, filed Jun. 14, 1996, now U.S. Pat. No. 5,912,171, issued Jun. 15, 1999, which is a continuation-in-part of U.S. Ser. No. 08/140,729, filed Oct. 20, 1993, now U.S. Pat. No. 5,658,782, issued Aug. 19, 1997, which is incorporated by reference herein in its entirety.

This invention was made with government support under National Institute of Health grant DA07595. The government has certain rights to this invention.

BACKGROUND OF THE INVENTION

1. Field of the Invention

This invention relates to amino acid transporters from mammalian species and the genes corresponding to such transporters. Specifically, the invention relates to the isolation, cloning and sequencing of complementary DNA (cDNA) copies of messenger RNA (mRNA) encoding a novel human amino acid transporter gene. The invention also relates to the construction of recombinant expression constructs comprising such cDNAs from a novel human amino acid transporter gene of the invention, said recombinant expression constructs being capable of expressing amino acid transporter protein in cultures of transformed prokaryotic and eukaryotic cells as well as in amphibian oocytes. Production of the transporter protein of the invention in such cultures and oocytes is also provided. The invention relates to the use of such cultures of such transformed cells to produce homogeneous compositions of the novel transporter protein. The invention also provides cultures of such cells and oocytes expressing transporter protein for the characterization of novel and useful drugs. Antibodies against and epitopes of the transporter protein are also provided by the invention.

2. Background of the Invention

The approximately 20 naturally-occurring amino acids are the basic building blocks for protein biosynthesis. Certain amino acids, such as glutamate and glycine, as well as amino acid derivatives such as γ-aminobutyric acid (GABA), epinephrine and norepinephrine, and histamine, are also used as signaling molecules in higher organisms such as man. For these reasons, specialized trans-membrane transporter proteins have evolved in all organisms to recover or scavenge extracellular amino acids (see Christensen, 1990, *Physiol. Rev.* 70: 43–77 for review).

These transporter proteins play a particularly important role in uptake of extracellular amino acids in the vertebrate brain (see Nicholls & Attwell, 1990, *TiPS* 11: 462–468). Amino acids that function as neurotransmitters must be scavenged from the synaptic cleft between neurons to enable continuous repetitive synaptic transmission. More importantly, it has been found that high extracellular concentrations of certain amino acids (including glutamate and cysteine) can cause neuronal cell death. High extracellular amino acid concentrations are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS; see Pines et al., 1992, *Nature* 360: 464–467).

Glutamate is one example of such an amino acid. Glutamate is an excitatory neurotransmitter (i.e., excitatory neurons use glutamate as a neurotransmitter). When present in excess (>about 300 $\mu$M; Bouvier et al., 1992, *Natures* 360: 471–474; Nicholls & Attwell, ibid.; >5 $\mu$M for 5 min.; Choi et al., 1987, *J. Neurosci.* 7: 357–358), extracellular glutamate causes neuronal cell death. Glutamate transporters play a pivotal role in maintaining non-toxic extracellular concentrations of glutamate in the brain. During anoxic conditions (such as occur during ischemia), the amount of extracellular glutamate in the brain rises dramatically. This is in part due to the fact that, under anoxic conditions, glutamate transporters work in reverse, thereby increasing rather than decreasing the amount of extracellular glutamate found in the brain. The resultingly high extracellular concentration of glutamate causes neuron death, with extremely deleterious consequences for motor and other brain functions, resulting in stroke and other instances of organic brain dysfunction.

This important role for amino acid transporters in maintaining brain homeostasis of extracellular amino acid concentrations has provided the impetus for the search for and development of compounds to modulate and control transporter function. However, conventional screening methods require the use of animal brain slices in binding assays as a first step. This is suboptiaaal for a number of reasons, including interference in the binding assay by non-specific binding of heterologous (i.e., non-transporter) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human transporter molecules in vitro would provide an efficient and economical means for rational drug design and rapid screening of potentially useful compounds.

Amino acid transporters are known in the art, and some of these proteins have been isolated biochemically and their corresponding genes have been recently cloned using genetic engineering means.

Christensen et al., 1967, *J. Biol. Chem.* 242: 5237–5246 report the discovery of a neutral amino acid transporter (termed the ACS transporter) in Erlich ascites tumor cells.

Makowske & Christensen, 1982, *J. Biol. Chem.* 257: 14635–14638 provide a biochemical characterization of hepatic amino acid transport.

Kanner & Schuldiner, 1987, *CRC Crit. Rev. Biochem.* 22: 1–38 provide a review of the biochemistry of neurotransmitters.

Olney et al., 1990, *Science* 248: 596–599 disclose that the amino acid cysteine is a neurotoxin when present in excess extracellularly.

Wallace et al., 1990, *J. Bacteriol.* 172: 3214–3220 report the cloning and sequencing of a glutamate/aspartate transporter gene termed gltP from *Escherichia coli* strain K12.

Kim et al., 1991, *Nature* 352: 725–728 report the discovery that a cationic amino acid transporter is the cell surface target for infection by ecotropic retroviruses in mice.

Wang et al., 1991, *Nature* 352: 729–731 report the discovery that a cationic amino acid transporter is the cell surface target for infection by ecotropic retroviruses in mice.

Maenz et al., 1992, *J. Biol. Chem.* 267: 1510–1516 provide a biochemical characterization of amino acid transport in rabbit jejunal brush border membranes.

Bussolati et al., 1992, *J. Biol. Chem.* 7: 8330–8335 report that the ASC transporter acts in an electrochemically neutral manner so that sodium ion co-transport occurs without disrupting the normal membrane potential of the cells expressing the transporter.

Engelke et al., 1992, *J. Bacteriol.* 171: 5551–5560 report the cloning of a dicarboxylate carrier from *Rhizobium meliloti*.

Guastella et al., 1992, *Proc. Natl. Acad. Sci. USA* 89: 7189–7193 disclose the cloning of a sodium ion and chloride ion-dependent glycine transporter from a glioma cell line that is expressed in the rat forebrain and cerebellum.

Kavanaugh et al., 1992, *J. Biol. Chem.* 276: 22007–22009 report that biochemical characterization of a rat brain GABA transporter expressed in vitro in *Xenopus laevis* oocytes.

Storck et al., 1992, *Proc. Natl. Acad. Sci. USA* 89: 10955–10959 disclose the cloning and sequencing of a sodium ion-dependent glutamatel aspartate transporter from rat brain termed GLASTI.

Bouvier et al., ibid., disclose the biochemical characterization of a glial cell-derived glutamate transporter.

Pines et al., ibid., report the cloning and sequencing of a glial cell glutamate transporter from rat brain termed GLT-1.

Kanai & Hediger, 1992, *Nature* 360: 467–471 disclose the cloning and sequencing of a sodium ion-dependent, high affinity glutamate transporter from rabbit small intestine termed EAAC1.

Arriza et al., 1992, *J. Biol. Chem.* 268: 15329–15332 disclose a gene for a novel neutral amino acid transporter.

Kong et al., 1993, *J. Biol. Chem.* 268: 1509–1512 report the cloning and sequencing of a sodium-ion dependent neutral amino acid transporter of the A type that is homologous to a sodium-ion dependent glucose transporter.

Arriza et al., 1994, *J. Neurosci.* 14: 5559–5569 disclose genes for three novel glutamate transporters.

Nicholls & Attwell, ibid., review the role of amino acids and amino acid transporters in normal and pathological brain functions.

SUMMARY OF THE INVENTION

The present invention relates to the cloning, expression and functional characterization of mammalian amino acid transporter genes. The invention comprises nucleic acids having a nucleotide sequence of a novel amino acid transporter gene. The nucleic acids provided by the invention each comprise a complementary DNA (cDNA) copy of the corresponding mRNA transcribed in vivo from the amino acid transporter gene of the invention. Also provided is the deduced amino acid sequences of the cognate protein of the cDNA provided by the invention.

This invention provides nucleic acids, nucleic acid hybridization probes, recombinant eukaryotic expression constructs capable of expressing the amino acid transporter of the invention in cultures of transformed cells and in amphibian oocytes, such cultures of transformed eukaryotic cells and such amphibian oocytes that synthesize the amino acid transporter of the invention, a homogeneous composition of the amino acid transporter protein, and antibodies against and epitopes of the amino acid transporter protein of the invention. Methods for characterizing this transporter protein and methods for using this protein and cells and oocytes expressing this protein for the development of agents having pharmacological uses related to this transporter protein are also provided by the invention.

In a first aspect, the invention provides a nucleic acid having a nucleotide sequence encoding a human excitatory amino acid transporter that is the EAAT4 transporter (SEQ ID No:1). In this embodiment of the invention, the nucleotide sequence includes 1734 nucleotides of the human EAAT4 cDNA comprising 1692 nucleotides of coding sequence, 8 nucleotides of 5' untranslated sequence and 34 nucleotides of 3' untranslated sequence. In this embodiment of the invention, the nucleotide sequence of the EAAT4 transporter is the nucleotide sequence depicted in FIG. 1 (SEQ ID No:1).

In another aspect, the invention comprises a homogeneous composition of the 61.6 kilodalton (kD) mammalian EAAT4 transporter and derivatives thereof, said size being understood to be the size of the protein before any post-translational modifications thereof. The amino acid sequence of the EAAT4 transporter and derivatives thereof preferably is the amino acid sequence of the human EAAT4 transporter protein shown in FIG. 2 (SEQ ID No:2). EAAT4 protein molecules provided by the invention are understood to have substantially the same biological properties as the EAAT4 protein molecule encoded by the nucleotide sequence described herein.

This invention provides both nucleotide and amino acid probes derived from the sequences herein provided. The invention includes probes isolated from either cDNA or genonic DNA, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of this transporter gene in various tissues of mammals, including humans. It is also an object of the present invention to provide nucleic acid hybridization probes derived from the sequences of the amino acid transporter gene of the invention to be used for the detection and diagnosis of genetic diseases. It is an object of this invention to provide nucleic acid hybridization probes derived from the DNA sequence of the amino acid transporter gene herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of amino acid transporter-specific antibodies, or used for competitors of amino acid transporter molecules for amino acid, agonist, antagonist or drug binding, or to be used for the production of inhibitors of the binding of agonists or antagonists or analogues thereof to such amino acid transporter molecules.

The present invention also provides antibodies against and epitopes of the mammalian amino acid transporter molecules of the invention. It is an object of the present invention to provide antibodies that are immunologically reactive to the amino acid transporter of the invention. It is a particular object to provide monoclonal antibodies against this amino acid transporter, most preferably the human excitatory amino acid transporter as herein disclosed. Hybridoma cell lines producing such antibodies are also objects of the invention. It is envisioned that such hybridoma cell lines may be produced as the result of fusion between a nonimmunoglobulin producing mouse myeloma cell line and spleen cells derived from a mouse immunized with a cell line which expresses antigens or epitopes of an amino acid transporter of the invention. The present invention also provides hybridoma cell lines that produce such antibodies, and can be injected into a living mouse to provide an ascites fluid from the mouse that is comprised of such antibodies. It is a further object of the invention to provide immunologically-active epitopes of the amino acid transporter of the invention. Chimeric antibodies immunologically reactive against the amino acid transporter protein of the invention are also within the scope of this invention.

The present invention provides recombinant expression constructs comprising a nucleic acid encoding an amino acid transporter of the invention wherein the construct is capable of expressing the encoded amino acid transporter in cultures of cells or amphibian oocytes transformed with the construct. Preferred embodiments of such constructs comprise the human EAAT4 cDNA (SEQ ID No.:1), the construct being capable of expressing the amino acid transporter encoded therein in cells and oocytes transformed with the construct or into which the construct has otherwise been introduced.

The invention also provides cultures cells transformed with the recombinant expression constructs of the invention, each such cultures being capable of and in fact expressing the amino acid transporter encoded in the transforming construct. The invention also provides amphibian oocytes into which a recombinant expression construct of the invention is introduced, each such oocyte being capable of and in fact expressing the amino acid transporter encoded in the transforming construct.

The present invention also includes within its scope protein preparations of prokaryotic and eukaryotic cell membranes containing the amino acid transporter protein of the invention, derived from cultures of prokaryotic or eukaryotic cells, respectively, transformed with the recombinant expression constructs of the invention. In a preferred embodiment, such preparations of cell membranes comprise the amino acid transporter protein of the invention.

The invention also provides methods for screening compounds for their ability to inhibit, facilitate or modulate the biochemical activity of the amino acid transporter molecules of the invention, for use in the in vitro screening of novel agonist and antagonist compounds. In preferred embodiments, cells, particularly amphibian oocytes transformed with a recombinant expression construct of the invention are contacted with such a compound, and the effect of the compound on the transport of the appropriate amino acid is assayed. Additional preferred embodiments comprise quantitative analyses of such effects. Also provided are assays that distinguish between the effect of such compounds on amino acid transport from effects of such compounds on chloride ion transport by the transporters of the invention.

The present invention is also useful for the detection of analogues, agonists or antagonists, heretofore known or unknown, of the amino acid transporters of the invention, either naturally occurring or embodied as a drug. In preferred embodiments, such analogues, agonists or antagonists may be detected in blood, saliva, semen, cerebrospinal fluid, plasma, lymph, or any other bodily fluid. In additional preferred embodiments, the invention provides methods for detecting and identifying analogues, agonists or antagonists that preferentially affect either the amino acid uptake function or the chloride ion channel function of the amino acid transporters of the invention.

Specific preferred embodiments of the present invention will become evident from the following more detailed description of certain preferred embodiments and the claims.

DESCRIPTION OF THE DRAWINGS

FIG. 1 illustrates the nucleotide (SEQ ID No.:1) sequence of the human EAAT4 excitatory amino acid transporter.

FIG. 2 illustrates the amino acid (SEQ ID No.:2) sequence of the human EAAT4 excitatory amino acid transporter.

FIG. 3 presents an amino acid sequence comparison between human EAAT4 (SEQ ID No.:2) and the previously-disclosed excitatory amino acid transporters EAAT1 (SEQ ID No.:4), EAAT2 (SEQ ID No.:6) and EAAT3 (SEQ ID No.:8).

FIG. 5 shows the pattern of expression of EAAT4 MRNA in human tissues; β-actin is shown as a control for amount of RNA in each lane.

DETAILED DESCRIPTION OF THE PREFERRED EMBODIMENTS

Figure 4:
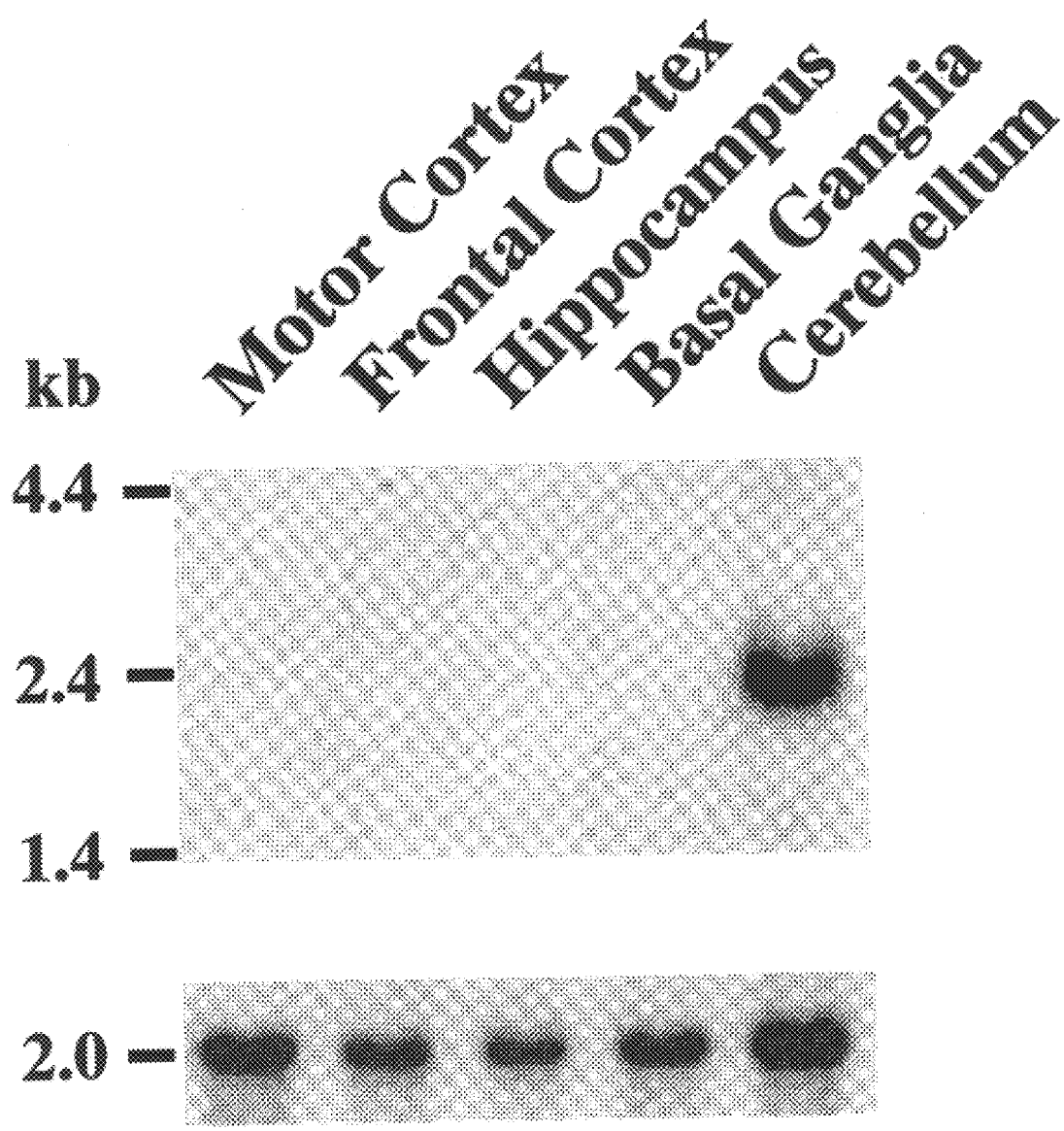
FIG. 4 shows the pattern of expression of EAAT4 mRNA in human brain tissue; β-actin is shown as a control for the amount of RNA in each lane.

The term "human amino acid transporter EAAT4" as used herein refers to proteins having substantially the same biological activity as the protein encoded by the nucleic acid depicted in FIG. 2 (SEQ ID No.:1). This definition is intended to encompass allelic variations in the EAAT4 sequence, either naturally occurring or the product of in vitro chemical or genetic modification. Each such variant will be understood to have essentially the same nucleotide sequence as the nucleotide sequence of the corresponding EAAT4 disclosed herein. Cloned nucleic acid provided by the present invention may encode EAAT4 protein of any species of origin, including, for example, mouse, rat, rabbit, cat, and human, but preferably the nucleic acid provided by the invention encodes EAAT4 receptors of mammalian, most preferably human, origin.

The term "excitatory amino acid" is intended to encompass naturally-occurring and synthetic amino acids such as L-aspartate and L-glutamate, as well as homologues, analogues or derivatives thereof. The terms is also intended to encompass agonists, antagonists and inhibitors of mammalian glutamate receptors.

The term "detectably labeled" is intended to encompass any reporter molecule capable of being detected by radiometric, fluorescent, spectrophotometric or other physical or chemical means. Particular examples include radiolabels, including but not limited to $^3H$ and $^{14}C$.

The term "chloride equilibrium potential" is intended to mean the membrane potentiat at which there is no detectable chloride ion flux across the cell membrane.

The nucleic acid hybridization probes provided by the invention comprise DNA or RNA having the nucleotide sequence of the amino acid transporters, depicted in FIG. 1 (SEQ ID No.:1), or any portion thereof effective in nucleic acid hybridization under stringency conditions sufficient to permit specific hybridization of the probe to a complementary nucleic acid sequence. Mixtures of such nucleic acid hybridization probes are also within the scope of this embodiment of the invention. Nucleic acid probes as provided herein are useful for detecting novel amino acid transporter genes related to the EAAT4 gene disclosed herein, specifically including homologous or syntenic transporter genes in non-human mammalian species. Nucleic acid probes as provided herein are also useful for detecting amino acid transporter gene expression in cells and tissues using techniques well-known in the art, including but not limited to Northern blot hybridization, in situ hybridization and Southern hybridization to reverse transcriptase—polymerase chain reaction (RT-PCR) product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with genetic disorders.

The production of proteins such as these amino acid transporter molecules from cloned genes by genetic engineering means is well known in this art. The discussion which follows is accordingly intended as an overview of this field, and is not intended to reflect the full state of the art.

DNA encoding an amino acid transporter may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from each of the amino acid transporters disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an amino acid transporter as provided herein. See U.S. Pat. Nos. 4,683,195 to Mullis et al. and 4,683,202 to Mullis.

The amino acid transporter protein of the invention may be synthesized in host cells, in particular amphibian oocytes, transformed with a recombinant expression construct comprising a nucleic acid encoding amino acid transporter cDNA. Such recombinant expression constructs can also be comprised of a vector that is a replicable DNA construct. Vectors are used herein either to amplify DNA encoding an amino acid transporter and/or to express DNA encoding an amino acid transporter gene. For the purposes of this invention, a recombinant expression construct is a replicable DNA construct in which a nucleic acid encoding an amino acid transporter is operably linked to suitable control sequences capable of effecting the expression of the amino acid transporter in a suitable host or host cell.

The need for such control sequences will vary depending upon the host selected and the transformation method chosen. Generally, control sequences include a transcriptional promoter, optional or ancillary transcription control sequences, such as transcription factor binding domains, enhancer sequences, and other eukaryotic "operator" sequences to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratible DNA fragments (i.e., fragments integratible into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pCMV5 (Andersson et al., 1989, *J. Biol. Chem.* 264: 8222–8229). Transformed host cells are cells which have been transformed or transfected with recombinant expression constructs made using recombinant DNA techniques and comprising nucleic acid encoding an amino acid transporter protein. Preferred host cells are *Xenopus laevis* oocytes, oocytes from other amphibian species, and COS-7 cells (Gluzman, 1981, *Cell* 2: 175–182). Transformed host cells may express the amino acid transporter protein, but host cells transformed for purposes of cloning or amplifying nucleic acid hybridization probe DNA need not express the transporter. When expressed, the amino acid transporter protein molecules of the invention will typically be located in the host cell membrane. See, Sambrook et al., ibid.

Cultures of cells derived from multicellular organisms are a desirable host for recombinant amino acid transporter protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Knise & Patterson, editors (1973). Examples of useful host cell lines are human 293 cells, VERO and HeLa cells, Chinese hamster ovary (CHO) cell lines, and W1138, BHK, COS-7, CV, and MDCK cell lines. COS-7 cells are preferred.

Certain other primary host cells, not subjected to prolonged tissue culture adaptation, can be used to produce the amino acid transporters of the invention, particularly amphibian oocytes. Amphibian oocytes are useful for expressing the mammalian excitatory transporters of this invention, most preferably oocytes from *Xenopus laevis* or other amphibian, which oocytes are used to provide cellsonvenient for the practice of some of the inventive methods disclosed herein.

Thus, the invention also provides a method for making the human EAAT4 amino acid transporters of the invention, and membrane preparations comprising this transporter, by introducing nucleic acid encoding the transporter into an appropriate prokaryotic, or preferably, eukaryotic, most preferably mammalian, cell that is capable of expressing the transporter protein.

The invention provides homogeneous compositions of the human EAAT4 amino acid transporter proteins produced by transformed eukaryotic cells as provided herein. Such a homogeneous compositions are intended to be comprised of the corresponding amino acid transporter protein that comprises at least 50–90% of the protein in such a homogeneous composition. The invention also provides membrane preparations from cells expressing the amino acid transporter protein as the result of transformation with a recombinant expression construct, as described herein.

Amino acid transporter protein made from cloned genes in accordance with the present invention may be used for screening amino acid analogues, or inhibitors, agonists or antagonists of amino acid transport, or for determining the amount of such agonists or antagonists in a solution of interest (e.g., blood plasma or serum). For example, host cells may be transformed with a recombinant expression construct of the present invention, an amino acid transporter expressed in those host cells, and the cells or membranes thereof used to screen compounds for their effect on amino acid transport activity. By selection of host cells that do not ordinarily express a particular amino acid transporter, pure preparations of membranes containing the transporter can be obtained.

The recombinant expression constructs of the present invention are useful in molecular biology to transform cells which do not ordinarily express a particular amino acid transporter to thereafter express this receptor. Such cells are useful as intermediates for making cell membrane preparations useful for transporter activity assays, which are in turn useful for drug screening. The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, *Cells* 51: 503–512; Bertling, 1987, *Bioscience Reports* 7: 107–112; Smnithies et al., 1985, *Nature* 317: 230–234.

Oligonucleotides of the present invention are useful as diagnostic tools for probing amino acid transporter gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding amino acid transporter gene, and potential pathological conditions related thereto.

The invention also provides antibodies that are immunologically reactive to the amino acid transporter protein or epitopes thereof provided by the invention. The antibodies provided by the invention may be raised, using methods well known in the art, in animals by inoculation with cells that express an amino acid transporter or epitopes thereof, cell membranes from such cells, whether crude membrane preparations or membranes purified using methods well known in the art, or purified preparations of proteins, including fusion proteins, particularly fusion proteins comprising epitopes of the amino acid transporter protein of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses the amino acid transporter provided by the invention, or any cell or cell line that expresses the amino acid transporter of the invention, or any epitope thereof, as a result of molecular or genetic engineering, or that has been treated to increase the expression of an endogenous or heterologous amino acid transporter protein by physical, biochemical or genetic means. Preferred cells are *E. coli* and insect SF9 cells, most preferably *E. coli* cells, that have been transformed with a recombinant expression construct of the invention encoding an amino acid transporter protein, and that express the transporter therefrom.

The present invention also provides monoclonal antibodies that are immunologically reactive with an epitope derived from an amino acid transporter of the invention, or fragment thereof, present on the surface of such cells, preferably *E. coil* cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an amino acid transporter of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an amino acid transporter, made by methods known to those of skill in the art.

The present invention also encompasses an epitope of an amino acid transporter of the invention, comprised of sequences and/or a conformation of sequences present in the transporter molecule. This epitope may be naturally occurring, or may be the result of proteolytic cleavage of a transporter molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an amino acid transporter-derived epitope. The chimeric antibodies embodied in the present invention include those that are derived from naturally occurring antibodies as well as chimeric antibodies made by means of genetic engineering technology well known to those of skill in the art.

The invention also provides methods for screening compounds for their ability to inhibit, facilitate or modulate the biochemical activity of the amino acid transporter molecules of the invention, for use in the in vitro screening of novel agonist and antagonist compounds. In preferred embodiments, cells, particularly amphibian oocytes transformed with a recombinant expression construct of the invention are contacted with such a compound, and the effect of the compound on the transport of the appropriate amino acid is assayed. Additional preferred embodiments comprise quantitative analyses of such effects. Also provided are assays that distinguish between the effect of such compounds on amino acid transport from effects of such compounds on chloride ion transport by the transporters of the invention.

The present invention is also useful for the detection of inhibitors, analogues, agonists or antagonists, heretofore known or unknown, of the amino acid transporters of the invention, either naturally occurring or embodied as a drug. In preferred embodiments, such inhibitors, analogues, agonists or antagonists may be detected in blood, saliva, semen, cerebrospinal fluid, plasma, lymph, or any other bodily fluid. In additional preferred embodiments, the invention provides methods for detecting and identifying inhibitors, analogues, agonists or antagonists that preferentially affect either the amino acid uptake function or the chloride ion channel function of the amino acid transporters of the invention.

The Examples which follow are illustrative of specific embodiments of the invention, and various uses thereof. They set forth for explanatory purposes only, and are not to be taken as limiting the invention.

EXAMPLE 1

Isolation of a Human Excitatory Amino Acid Transporter cDNA

Excitatory amino acid transporters EAAT1, EAAT2 and EAAT3 have been disclosed in co-owned and co-pending U.S. Ser. No. 08/140,729, filed Oct. 20, 1993, now U.S. Pat. No. 5,658,782, issued Aug. 19, 1997, which is incorporated by reference herein in its entirety.

In order to clone a novel human excitatory amino acid transporter, cDNA was prepared from human cerebellar MRNA and amplified in vitro using a pair of degenerate primers derived from two regions of sequence similarity between the EAAT1, EAAT2 and EAAT3 genes previously disclosed. Briefly, total RNA was isolated using the method of Chomczynski & Sacchi (1987, *Anal. Biochem.* 16: 156–159), wherein the tissue is disrupted and solubilized in a solution containing guanidinium isothiocyanate and the RNA purified by phenol/chloroform extractions. Total cellular RNA thus isolated was then enriched for poly ($A^+$) MRNA by oligo (dT) chromatography. A mixture of oligo (dT)-primed and random-primed mRNA was converted to cDNA using the Superscript Choice System (Bethesda Research Labs, Gaithersburg, Md.). 10 ng of this cerebellum-derived cDNA preparation was then amplified using the following degenerate oligonucleotide primers:

Sense primer:
  5'-CGCGGGTACCAA(T/C)CT(C/G)GT(C/A/G)(G/C)A(G/A)GC(T/C)TG(T/C)TT(T/C)-3' (SEQ ID NO:9);

Antisense primer:
  5'-CGCGTCTAGA(T/C)TG(A/G/T)GC(A/GmAT(A/G)AA(A/G)A(T/C)(G/T/C)GC(A/G/T)GC-3' (SEQ ID NO:10).

PCR amplification was performed for 35 cycles, each cycle comprising 1 minute at 94° C., 1 min at 47° C. and 2 minutes at 72° C. using Vent polymerase (New England Biolabs, Beverly, Mass.). Following the PCR, the product of the amplification reaction was purified using standard techniques (Saiki et al., 1988, *Science* 239: 487–491).

Novel candidate clones were identified by the following hybridization strategy. Bona fide transporter cDNAs were identified by hybridization with the following degenerate oligonucleotide probe for a highly conserved coding sequence:
  5'-CTGRGCRATGAARATGGCAGCCAGGGCYTCAT ACAGGGCTGTGCCRTCCATGTTRATGGTRGC-3' (SEQ ID No.:1)
(See Arriza et al., 1992, ibid.). Those transporter cDNAs previously isolated (i.e., encoding EAAT1, EAAT2, EAAT3, ASCT1) were identified by specific hybridization with their previously-isolated cDNA probes under high stringency conditions (e.g., 0.1×SSC (standard citrate saline)/1% SDS (sodium dodecyl sulfate) at 65° C. (see Sambrook et al., 1990, *Molecular Cloning: A Laboratory Manual* (Cold Spring Harbor Press: New York))). cDNAs that hybridized with the oligonucleotide but did not correspond to previously isolated cDNAs were characterized by nucleotide sequence analysis.

A novel clone similar to the previously-identified glutamate transporters was identified. This novel PCR amplification product was used to screen a motor cortex MnRNA prepared using standard techniques (see Sambrook et al., ibid.). Total RNA was isolated using the method of Chomczynski & Sacchi as above, and then enriched for poly ($A^+$) MRNA by oligo (dT) chromatography. A mixture of oligo (dT)-primed and random-primed mRNA was converted to cDNA using the Superscript Choice System and the cDNA was then ligated into the cloning vector λZAPII (Strategene, La Jolla, Calif.), packaged into phage heads using commercially-available packaging extracts (Sutegene) and used to infect E. coli. Lawns of infected bacterial cells were used to make plaque lifts for hybridization using standard conditions (see Sambrook, et al., ibid.).

This cDNA library was hybridized with the $^{32}$P-labeled PCR amplification product described above. Hybridization was performed at 50° C. in a solution containing 0.5M $Na_2HPO_4$ (pH 7.15)/7% sodium dodecyl sulfate (SDS) and the filters were washed at 60° C. in 2×SSPE (0.36M NaCL/ 20 mM sodium phosphate (pH 7.7)/2 mM ethylenediamine tetraacetic acid (EDTA)) and 1% SDS. Hybridizing clones were identified by autoradiography at −70° C. using tungsten-containing intensifying screens (DuPont-NEN, Wilmington, Del.).

Figure 3:
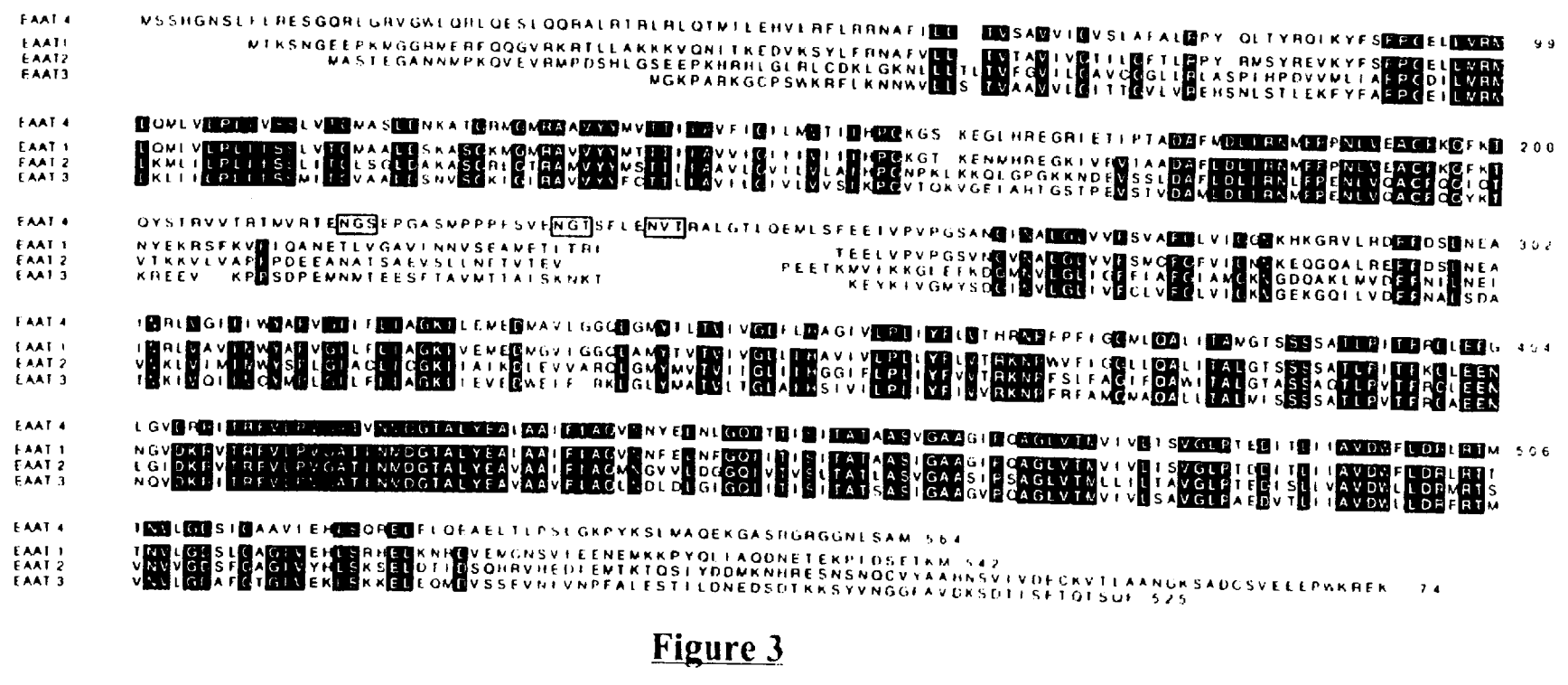

Two independent clones containing 2.2 and 2.3 kilobase pair (kb) cDNA inserts were isolated. cDNA inserts were excised from the cloning vector in vivo by superinfection with a defective filamentous phage that recognizes and excises cloned insert sequences along with adjacent modified phage replication-form sequences (termed pBluescript SK and available from Strategene). Each clone was then sequenced using the dideoxy-hain termination method of Sanger et al. (1977, Proc. Nati. Acad. Sci. USA 74: 5463), using Sequenase 2.0, a modified form of bacteriophage T7 DNA polymerase (U.S. Biochemical Corp., Cleveland, Ohio). The two independent clones contained identical long open reading frames, and were identical in those regions of the 3' untranslated sequences analyzed. Each clone had a distinct 5' untranslated sequence but were identical in the 8 nucleotides upstream of the putative translation start site. This observation may be indicative of alternative RNA splicing in the 5' untranslated region of the EAAT4 gene. The 1734 nucleotide sequence of the human EAAT4 cDNA shown in FIG. 1 includes the conserved 8 nucleotides of the 5' untranslated region, 34 nucleotides of the 3' untranslated region downstream of the translation stop codon, and 1692 nucleotides of coding sequence comprising 564 amino acids (FIG. 2 and FIG. 3).

The EAAT4 amino acid sequence (SEQ ID No.:2; shown in FIG. 2) was found to exhibit similarity to other known glutamate transporter subtypes (an amino acid sequence comparison is shown in FIG. 3). An amino acid comparison between these 4 human glutamate transporters showed 65%, 41% and 48% sequence identity (respectively) between EAAT4 and EAAT1, EAAT2 and EAAT3 (shown in FIG. 3 by shaded boxes). Both the amino and carboxyl termini were found to be divergent between these transporter proteins, and diversity was also found in the extracellular domains of these putative protein sequences, which contain conserved potential N-glycosylation sites (shown in FIG. 3 by open boxes). It was noted that previously-identified sequence (comprising the amino acids—AA(I/V)FIAQ—) that was highly conserved in the glutamate transporters was also present in EAAT4 (at positions 434–440 of the EAAT4 amino acid sequence shown in FIG. 2). 6–10 putative transmembrane domains were found using the algorithm of Eisenberg et al. (1984, J. Molec. Biol. 179: 125–142). On the basis of these data EAAT4 was determined to encode a related but distinct and novel member of the excitatory amino acid transporter family.

EXAMPLE 2

Tissue Distribution of Amino Acid Transporter Expression

The tissue distribution of MRNA corresponding to expression of the EAAT4 amino acid transporter disclosed herein was determined in various tissues by Northern hybridization experiments (see Sambrook et al., ibid.). The results of these experiments are shown in FIGS. 4 and 5.

A panel of tissue samples was examined by Northern hybridization analysis performed under high stringency conditions as follows. A nylon filter containing 2 µg human peripheral tissue poly(A)$_+$ RNA was obtained from Clonetech Laboratories (Palo Alto, Calif.), and a similar filter was prepared containing human brain region RNA as follows. Total RNA was isolated from human brain region tissue obtained from the Oregon Brain Repository and 20 µg/region were size-fractionated by denaturing formaldehyde agarose gel electrophoresis (see Sambrook et al., ibid.). Fractionated RNA was then transferred to a nylon filter using the Northern blot/capillary-osmotic technique. Northern hybridization of both filters was performed individually with a $^{32}$P-labeled 1.7 kb EAAT4-specific probe prepared by random-primed synthesis (Boehringer Mannheim, Indianapolis, Ind.) using α-$^{32}$P-labeled dCTP. Filters were hybridized overnight at 42° C. individually with each radiolabeled probe (at a concentration of $10^6$ cpm/nL) in a solution of 5×SSPE/50% formarnide/7.5×Denhardt's solution (comprising 0.15 g/100 mL each of Ficoll, polyvinylpyrrolidone and bovine serum albumin)/2% SDS and 100 µg/mL denatured salmon-sperm DNA. Following hybridization, filters were washed twice for 30 min at room temperature in 2×SSPE/0.1% SDS and twice for 20 min at 50° C. in 0. 1×SSPE/0.1% SDS. Hybridizing RNAs were visualized by autoradiography at −70° C. using intensifying screens. The filters were subsequently re-probed as described with a radiolabeled human β-actin probe (Clonetech) as a positive control.

The results of these experiments, shown in FIGS. 4 and 5, demonstrate that EAAT4 transporter has a distribution distinct from other transporters isolated to date. FIG. 4 shows the distribution of these amino acid transporter transcripts in different human brain regions. Expression of the 2.4 kb EAAT4 mRNA was detected only in cerebellum using this Northern blot assay. However, a more sensitive polymerase chain reaction-based assay revealed EAAT4 expression in brain stem, cortex and hippocampus, albeit at much lower levels than those seen in cerebellum.

FIG. 5 illustrates expression of the EAAT4 transporter in human heart, brain, placenta, lung, liver, muscle, kidney and pancreas. The size (in kb) of the transcripts corresponding to expression of this transporter are displayed along the right-hand border of each panel. As is seen from these autoradiographs, EAAT4 was found to be expressed predominantly in brain and placenta as a single, 2.4 kb transcript, consistent with the size of the isolated cDNA clones.

These results support the conclusion that the amino acid transporter of the invention may play an important role in normal brain function, and that disruption of amino acid transport by this transporter may be important determinants in organic brain dysfunction, as a result of ischemia or anoxia. Moreover, because of the presumed role of the cerebellum in motor learning, the abundant expression of EAAT4 mRNA in the cerebellum suggests that this protein may be significant in both normal and dysfunctional (e.g., ataxia and related syndromes) motor coordination.

EXAMPLE 3

Functional Expression of the EAAT4 Amino Acid Transporter Gene in Xenopus Oocytes The sequence similarity between EAAT4 and the previously-identified glutamate transporters EAAT1, EAAT2 and EAAT3 suggested that the protein encoded by the EAAT4 cDNA was an amino acid transporter. The ability of the EAAT4 gene product to transport amino acids, and the identity of which amino acids might be transported by this gene product, was assayed in Xenopus oocytes following microinjection of in vitro synthesized EAAT4 RNA.

Briefly, the coding sequence of the EAAT4 cDNA was isolated with unique flanking restriction sites using a PCR-based assay. In this assay, each of the complementary primers used for PCR amplification of the coding sequence contained a sequence encoding a unique restriction enzyme recognition site at the 5' terminus of each PCR primer. For EAAT4, the sense primer contained a Hindi recognition sequence (A↓AGCTI), and the antisense primer contained an XbaI recognition sequence (T↓CTAGA) at their respective 5' termini. Each of the PCR primers used for amplifying EAAT4 sequences had the following sequence:

EAAT4 sense primer:
5'-GCGCGTCGACAAGCTTGCCATGCAACAGCC TGTT-3' (SEQ ID NO:12);

EAAT4 antises primer:
5'-GCGCTCTAGATCAGCCCACGGTCAGTTG-3' (SEQ ID NO:13).

PCR amplification was performed for 30 cycles, each cycle comprising 30 seconds at 94° C., 30 seconds at 55° C. and 1 minute at 72° C. Following the PCR, the product of the amplification reaction was purified using standard techniques (Sailki et al., 1988, Science 239: 487–491). The DNA then digested with the restriction enzymes HindIII and XbaI and then cloned into the polylinker of an oocyte transcription vector (pOTV; see Arriza et al., 1992, ibid.). Capped RNA was synthesized from linearized plasmid employing bacteriophage T7 RNA polymerase (mMessage mMachine; Ambion, Austin, Tex.), diluted with water to a concentration of 400 µg/mL, and 50 nL of this EAAT4 RNA was injected into defolliculated stage V or VI oocytes. Oocytes were prepared as described (Quick and Lester, 1994, Methods in Neuroscience 19: 261–279) and maintained at 17° C. for up to 5 days.

Amino acid transport in these oocytes was assayed at room temperature 3–5 days post injection using various concentrations of [$^3$H]-L-aspartate or [$^3$H]-L-glutamate (obtained from New England Nuclear, Boston, Mass.) in ND96 buffer (96 mM NaCl/2 mM KCl/1.8 mM CaCl$_2$/1 m MgCl$_2$/5 mM Hepes, pH 7.5).

Two electrode voltage clamp recordings from EAAT4-expressing oocytes were performed at room temperature using glass microelectrodes filled with 3M KCl solutions (resistance<1 MΩ) and a Ag/AgCl pellet bath ground or an active bath probe. An Axon GeneClamp 500 amplifier was used with Digidata 1200 interfaces. The pClamp suite of programs (Axon Instruments, Foster City, Calif.) was used to control stimulation parameters, for data acquisition and analysis. MacLab data acquisition software and a MacLab/ 2e interface (ADI Instnunents, Milford, Mass.) were used to record electrophysiological experiments. 3M KCl/agar bridges were used to avoid offset voltages associated with buffer changes. Oocytes were continuously superfused with ND96 or ion substituted ND96 during the recording session.

The properties of EAAT4 cRNA-injected oocytes were examined by analysis of excitatory amino acid-induced currents in voltage-clamped oocytes. In these experiments, the maximum current of depolarization ($I_{max}$) and the transport constant ($K_m$) induced by treatment with a variety of putative EAAT4 transporter substrates was determined. The results of these experiments are shown in Table I. Injected oocytes were also incubated with a mixture of radiolabeled amino acid ([$^3$H]-L-glutamate (17.8 Ci/mmol) or [$^3$H]-D-aspartate (15.5 Ci/mmol); Dupont-NEN) and non-radiolabeled amino acid at increasing doses of 0.1, 0.3, 1, 3, 10 and 100 µM for 10 min. for determination of the $V_{max}$ and $K_m$ of substrate flux. After incubation, the cells were washed four times with ice-cold PBS, solubilized with a solution of 0.1 % sodium dodecyl sulfate (SDS) and the amount of radioactivity associated with the cells determined using standard liquid scintillation counting methods.

Application of L-aspartate or L-glutamate to EAAT4 cRNA-injected, voltage-clamped oocytes induced dose-dependent, saturable inward currents; no such currents were observed in control, mock-injected oocytes. Flux experiments showed that oocytes injected with the EAAT4 excitatory amino acid transporter-encoding cRNA accumulated significantly-higher (about 30-fold higher) saturable, sodium-dependent uptake of [$^3$H]-L-aspartate and [$^3$H]-L-glutamate than did mock-injected oocytes. The maximal currents elicited by other test compounds were normalized relative to the maximal current obtained with a saturating dose (100 µM) of L-aspartate in the same oocyte such that these determinations were independent of the level of EAAT4 expression in individual oocytes. For this normalization, the current elicited by a maximal dose of L-aspartate was measured before and/or after dose response determinations for each compound and given a normalized $I_{max}$ value of 1.0. No compound tested induced a depolarizing current in uninjected oocytes or water-injected oocytes. The course of uptake of 10µM radioactive aspartate was found to be linear for at least 20 min in assays performed at room temperature. The $K_m$ values derived from the current measurements as well as radiolabel substrate uptake experiments, as shown in Table I, were about 10-fold lower than those found for previously-disclosed members of the EAAT transporter family. Maximal flux and current measurements (Table 1) indicated a discrepancy between the maximal transport and maximal current generated by L-aspartate and L-glutamate. Although L-aspartate produced a current significantly larger than L-glutamate (1.0 versus 0.37, respectively), its maximal transport rate is significantly lower than that of L-glutamate (3.26 versus 5.72). This data suggested that the substrate elicited currents observed are not a direct reflection of substrate transport and that the two phenomena may be uncoupled.

Structural analogues of glutamate, including L-trans-2, 4pyrrolidine dicarboxylic acid, L-quisqualate and L-α-amino adipate, also elicited currents of varying magnitude in EAAT4-injected oocytes, while kainic acid, which blocks glutamate transport in some brain regions, was found to be ineffective in either eliciting a current or blocking an L-aspartate induced current at concentrations as high as 5 mM. These properties of the EAAT4 transporter are consistent with glutamate uptake activity previously reported for cerebellum and are consistent with localization of EAAT4 expression primarily in cerebellar tissues.

Figure 6A:
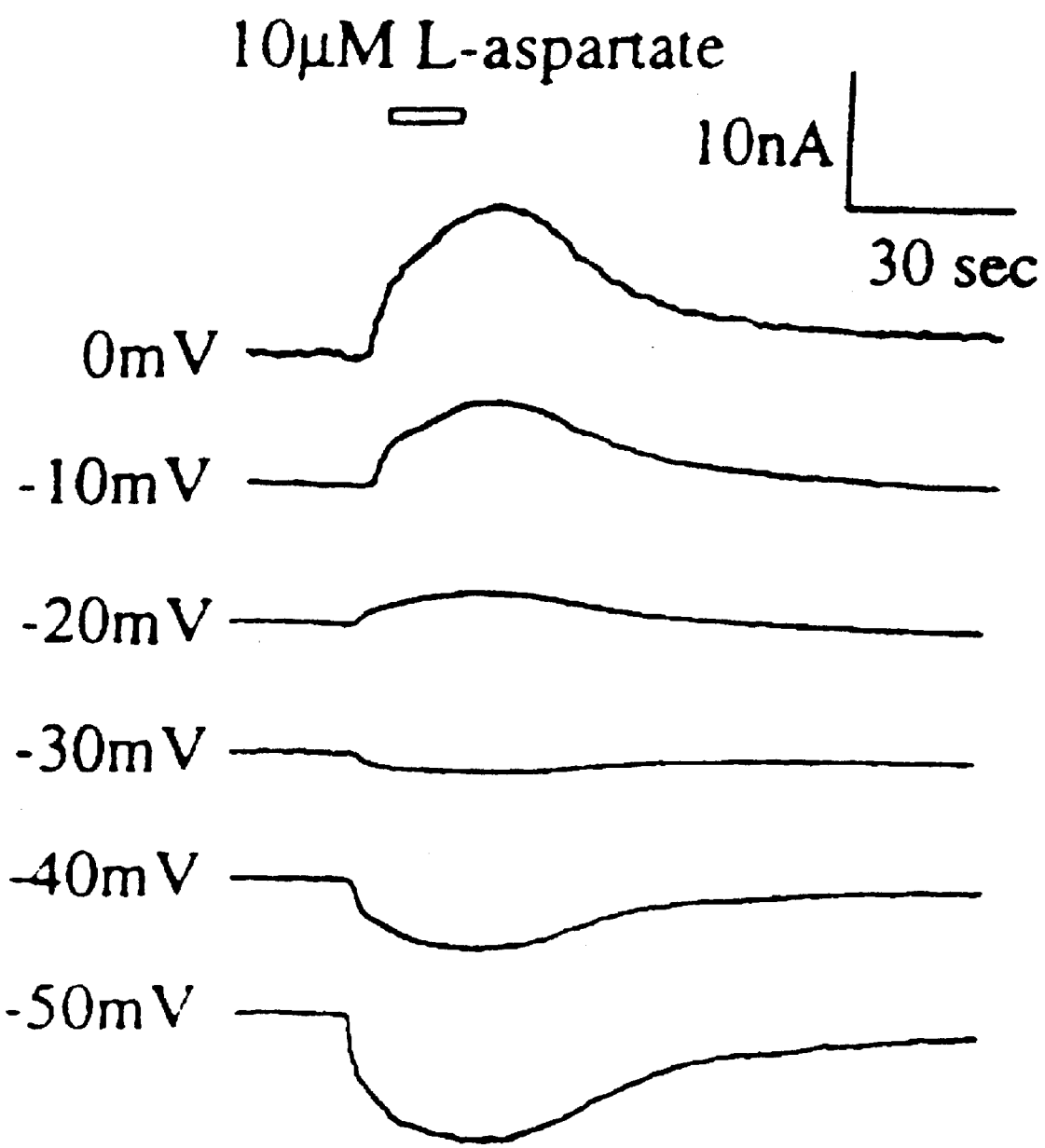
FIG. 6A illustrates transmembrane electrochemical currents in Xenopus laevis oocytes microinjected with RNA encoding EAAT4 cRNA and contacted with 10 μM L-aspattate at varying voltage-clamped voltages. The magnitude of the induced current and the time course of induction are shown with reference to the indicator bars in the upper right-hand corner of the Figure.
Figure 6B:
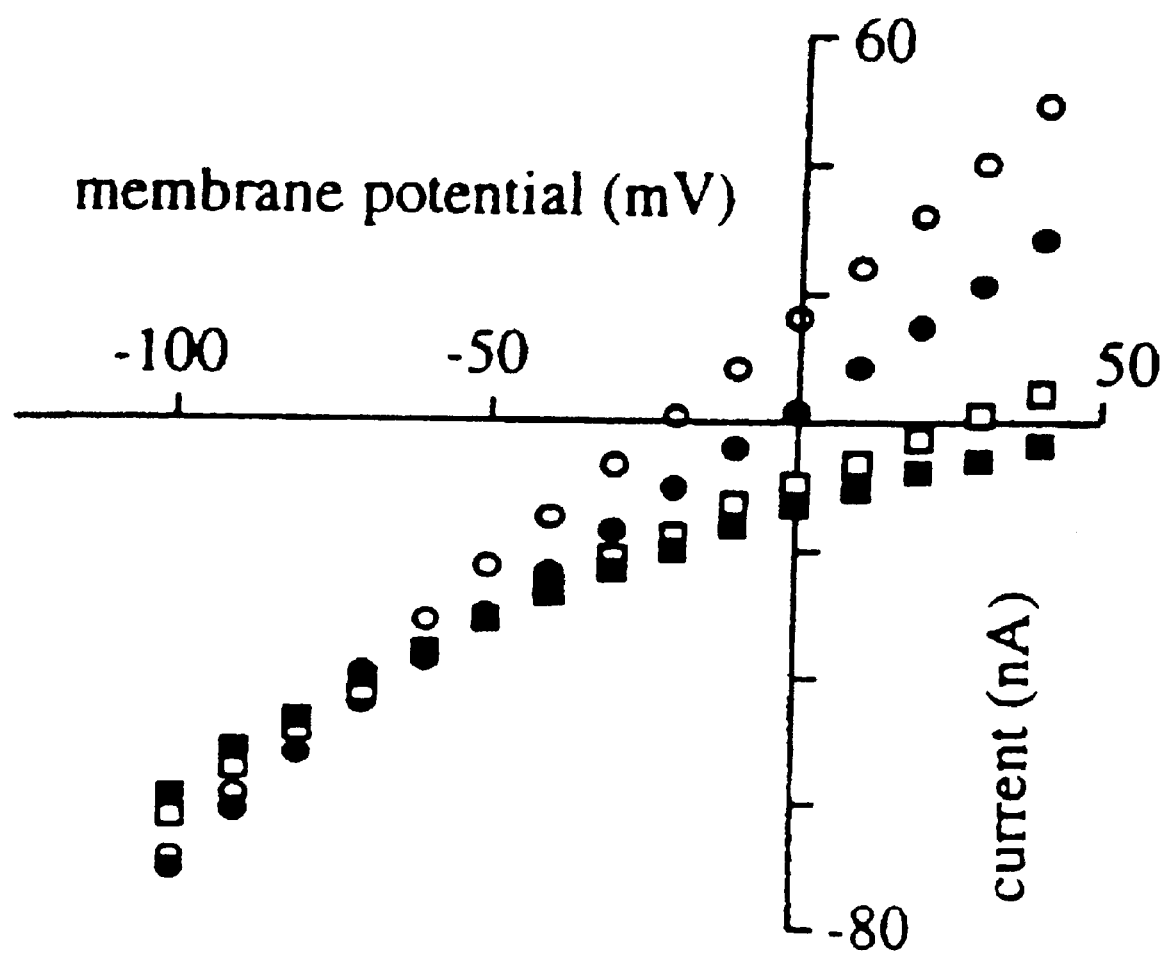
FIG. 6B is a graph showing the relationship between the magnitude of the applied voltage clamp and the induced current in the presence of increasing amounts of gluconate ion in substitution for chloride ion. Open circles correspond to 104 mM chloride ion (no gluconate ion present), closed circles correspond to 56 mM chloride ion, open squares correspond to 20 mM chloride ion and closed squares correspond to 0 mM chloride ion (i.e., chloride ion is substituted entirely by gluconate ion).

Further characterization of the electrophysiology of EAAT4 accompanying aspartate transport revealed a significant difference between EAAT4 and the previously-isclosed members of the EAAT transporter family. L-glutanate- and L-aspartate-induced currents found in voltage-clamped oocytes expressing these other members of the EAAT family exhibited strong inward rectification (i.e., currents were induced that were preferentially inward) and were not found to reverse below +40 mV. In contrast, 10 $\mu$M L-aspartate was found to induce an outward current in EAAT4-injected oocytes at voltages more positive than~−20 mV. Results of experiments demonstrating this phenomenon are shown in FIG. 6A. In FIG. 6B it is shown that the voltage-ependence of the L-aspartate induced current is approximately linear from about −100 mV to about +40 mV, reversing at −22±1.6 mV (n=18). This value is approximately equal to the previously-reported equilibrium potential of chloride ion in native Xenopus oocytes (−24 mV; see Barish, 1983, *J. Physiol.* (London) 342: 309–325).

Figure 6C:
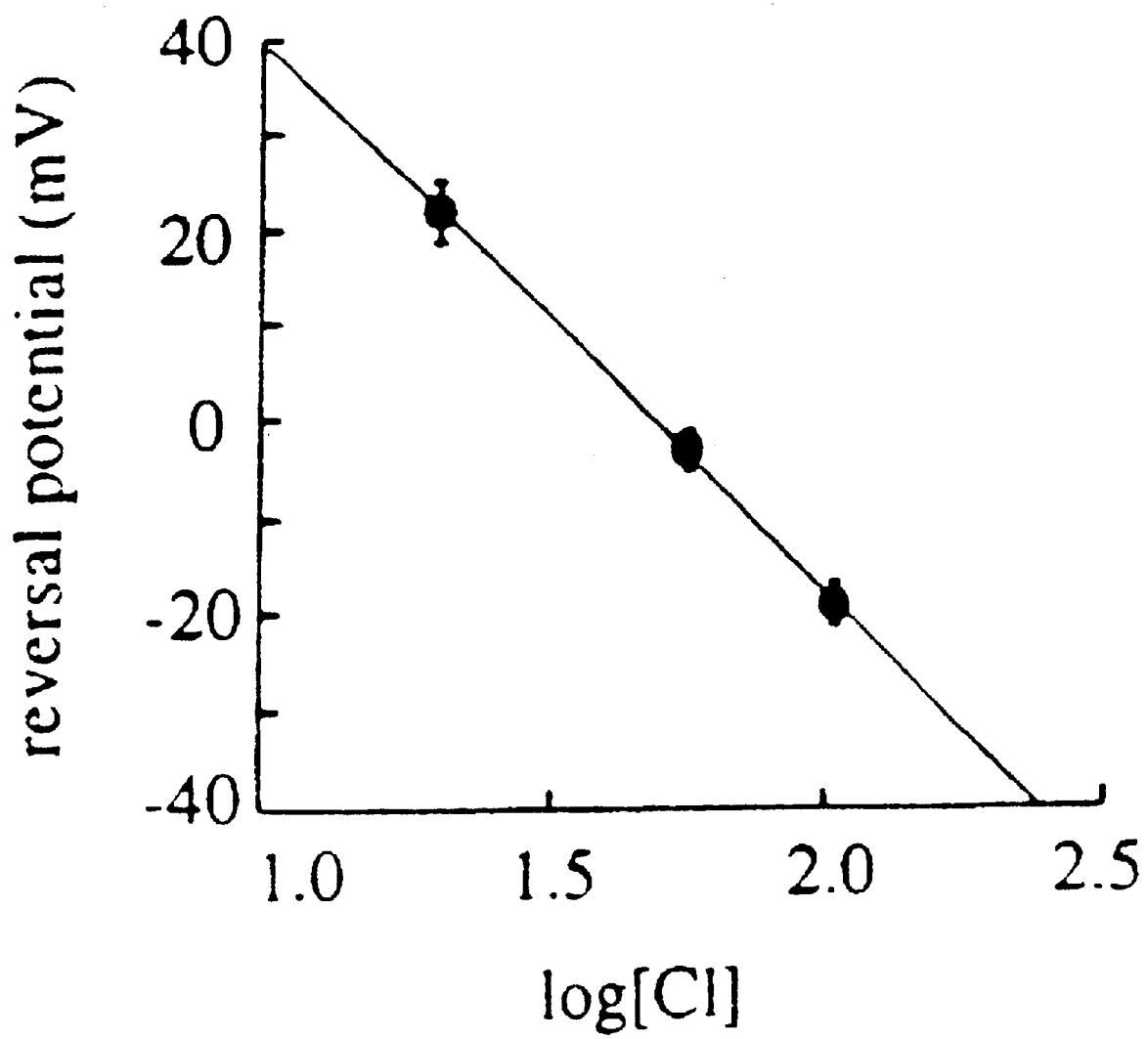
FIG. 6C is a sernilogarithrnic plot of the reversal potential versus the log of the chloride ion concentration, showing that the application of excitatory amino acids to EAAT4 induces a large chloride ion current.

To investigate the significance of this coincidence, the chloride ion-dependence was assayed by substituting chloride ion with gluconate ion. The reversal potential of the L-aspartate induced currents were found to shift by 57±1.5 mV for every ten-fold change in chloride ion concentration, as shown in FIGS. 6B and 6C. This result is in accord with theoretical predictions of the Nernst equation for chloride-ion selective conductance. Similar results were obtained using L-glutamate (reversal potential shifted 50±2 mV for every ten-fold change in chloride ion concentration). The difference in the reversal potential shift seen with L-glutamate and L-aspartate (50 mV versus 57 mV) results from differences in their relative efficacies as transport substrates (Glu>Asp) and as elicitors of the chloride conductance (Asp>Glu).

Figure 6D:
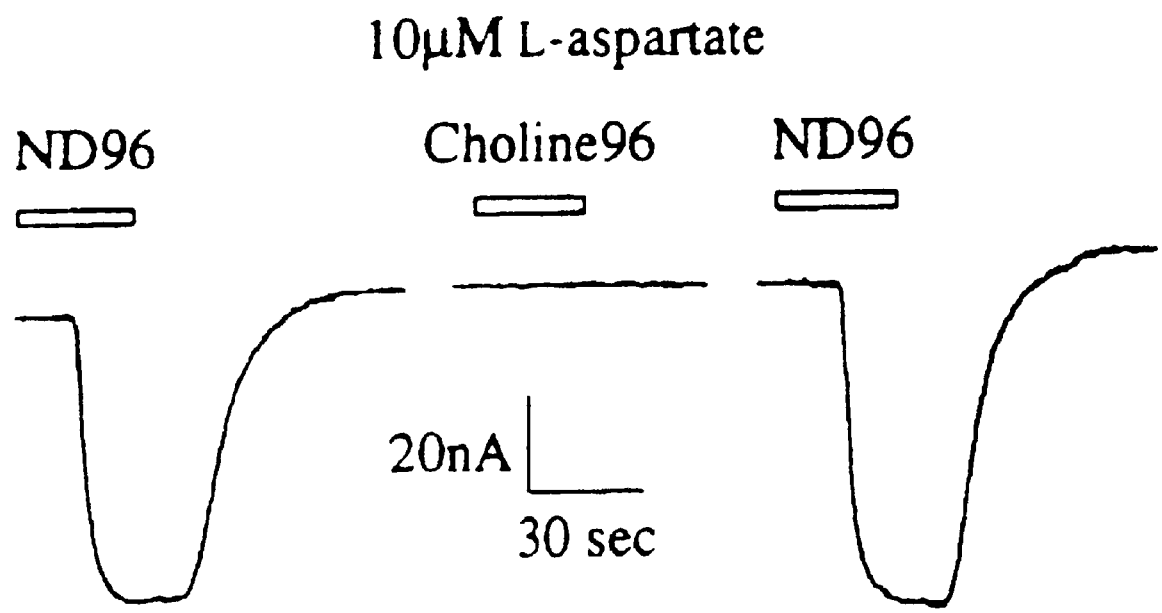
FIG. 6D illustrates transmembrane electrochemical currents in Xenopus oocytes microinjected with RNA encoding EAAT4 cRNA and contacted with 10 μM L-aspartate in the presence and absence of sodium ion in the perftisate. The magnitude of the induced current and the time course of induction are shown with reference to the indicator bars in the upper right-hand corner of the Figure.

Complete removal of chloride by substitution with gluconate ion abolished the L-aspartate induced outward currents at depolarized potentials (see FIG. 6B). However, L-aspartate transport at +60mV in the absence of chloride ion ($V_{max}$=4.7±0.3 fmol/s, n=8) was not significantly different than transport in the presence of chloride ion ($V_{max}$= 5.9±0.3 fmol/s, n=8), indicating that transport is not dependent on external chloride ion. In contrast, substitution of sodium ions with choline completely and reversibly abolished L-aspartate-induced currents, consistent with the sodium dependence of uptake and with the sodium-dependent activation of chloride conductance by excitatory amino acids (FIG. 6D).

TABLE I

Pharmacological Properties of EAAT4 Substrate Flux and Conductance Currents

| Amino Acid | $K_m$ ($\mu$M) | |
|---|---|---|
| | | $V_{max}$ |
| [$^{3H}$]-L-aspartate | 0.97 ± 0.29 | 3.26 ± 0.06 |
| [$^{3H}$]-L-glutamate | 2.49 ± 0.87 | 5.72 ± 0.52 |
| | | $I_{max}$ |
| L-aspartate | 1.84 ± 0.46 | 1.0 |
| L-glutamate | 3.3 ± 0.4 | 0.37 ± 0.07 |

TABLE I-continued

Pharmacological Properties of EAAT4 Substrate Flux and Conductance Currents

| Amino Acid | $K_m$ ($\mu$M) | |
|---|---|---|
| D-aspartate | 2.5 ± 0.3 | 1.0 ± 0.1 |
| L-$\alpha$-adipate | 168 ± 11 | 0.75 ± 0.02 |
| L-quisqualate | 99 ± 11 | 0.47 ± 0.06 |
| L-homocysteate | 403 ± 72 | 0.83 ± 0.05 |
| PDC* | 2.6 ± 0.4 | 0.41 ± 0.01 |
| Kainic acid | >5000 | undetectable |

Figure 7A:
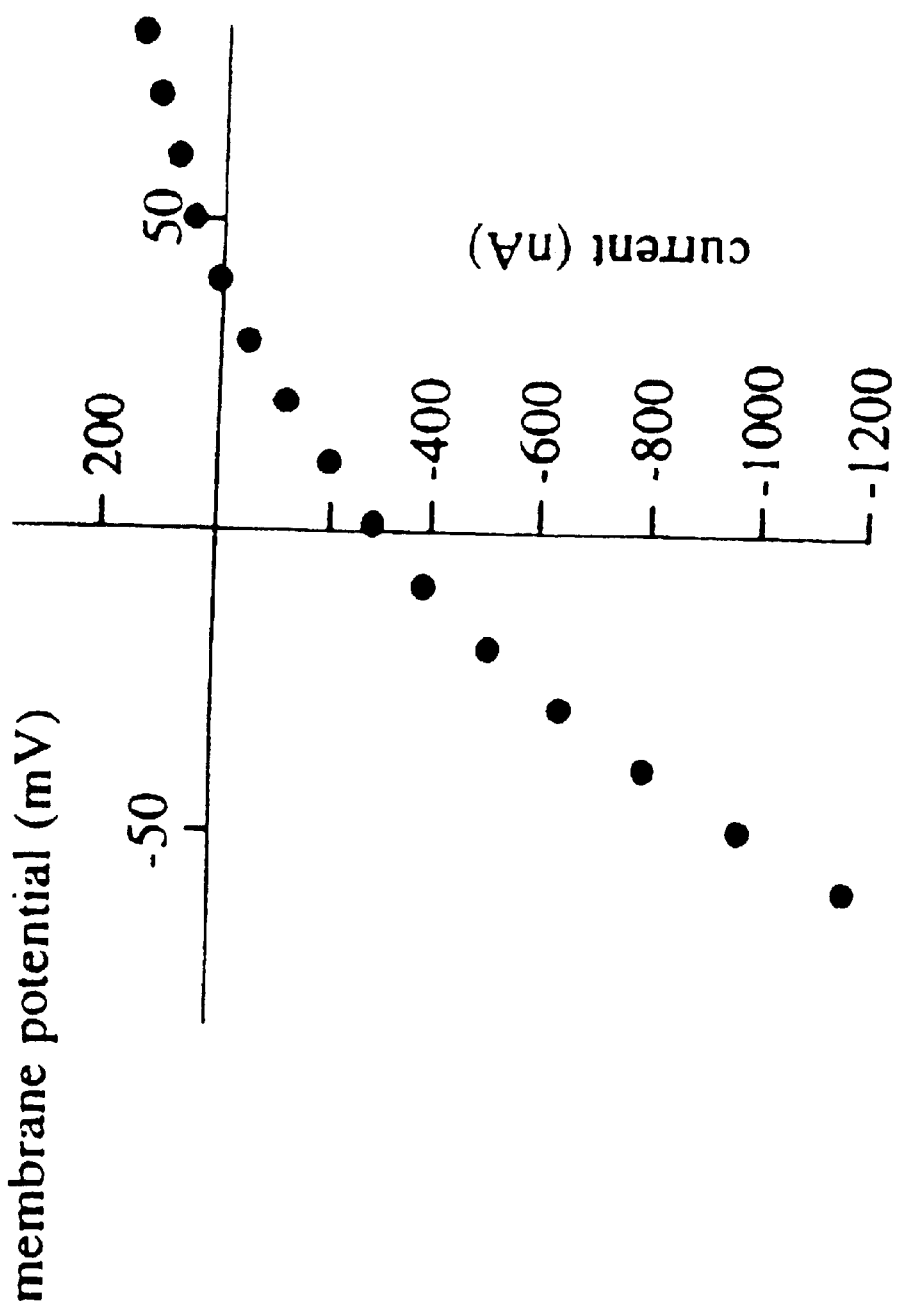
FIG. 7A is a graph illustrating the current-voltage (I–V) relationship typical for EAAT1, EAAT2, and EAAT3, illustrated for EAAT-2. In this example, the application of L-glutamate to EAAT2, there is inward rectification of the current, and outward currents are seen only at membrane potentials more positive than +40 mV.
Figure 7B:
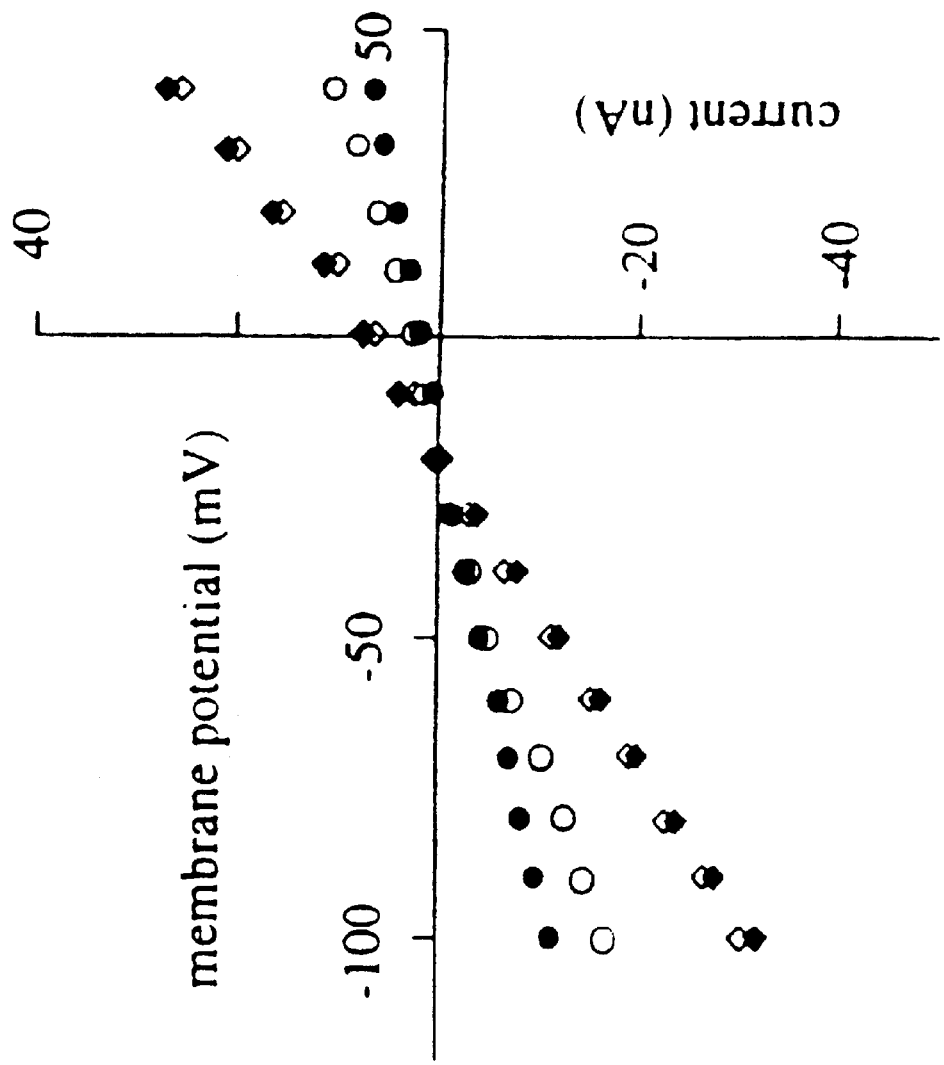
FIG. 7B is a graph showing the concentration and voltage dependence of L-aspartate induced currents in EAAT4. The current is dose-dependent, linear, and reverses (becomes outward) at a membrane potential of ~–20 mV. L-aspartate concentrations shown are 0.3 μm (filled circles), 1 μM (open circles), 10 μM (open diamonds), and 100 μM (filled diamonds).

NOTE: data is expressed as the mean of at least 5 determinations ± standard error.
*= L-trans-2,4-pyrrolidine dicarboxylic acid $V_{max}$ was determined by least squares fit to the equation:

$$V=V_{max}\times([S]/(K_m+[S])$$

where $V_{max}$ is the maximal transport rate and $K_m$ is the transport constant The magnitude of the induced chloride conductance in EAAT4 distinguishes it from EAAT1, EAAT2, or EAAT3. EAAT1 through EAAT3 have large transport currents with small or undetectable chloride conductances, such that their current/voltage profiles show inward rectification, i.e., at positive potentials the current is reduced but is not reversed or outward at potentials less than +40 mV. This is illustrated by the I-V profile for EAAT2 shown in FIG. 7A. In contrast, the EAAT4 I-V profile does not show rectification; rather, the profile is linear with the reversal potential ~−20 mV, and the reversal potential is constant regardless of the dose of L-aspartate applied (FIG. 7B). Flux studies under voltage-clamp conditions were conducted and fit to the Faraday equation. It was concluded that greater than 95 % of the L-aspartate induced current in EAAT4-expressing oocytes can be attributed to chloride conductance.

Figure 7C:
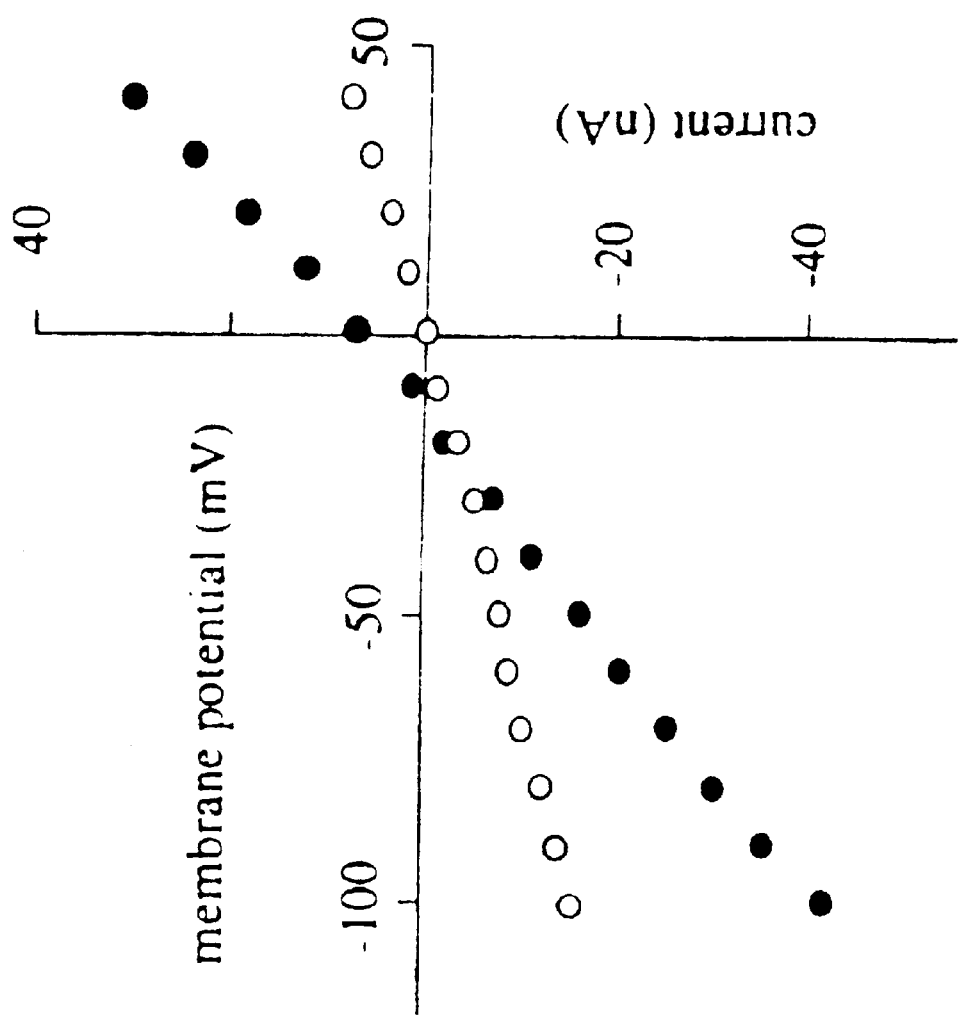
FIG. 7C is a graph comparing the current-voltage relationships of L-aspartate and L-glutamate, for concentrations of 100 μM L-aspartate (filled circles) and 100 μM L-glutamate (open circles).

L-aspartate and L-glutamate were found to differ in the degree to which they elicit either the transport current component or the chloride conductance component of EAAT4 (FIG. 7C). This is reflected by the fact that, although the reversal potential for L-aspartate was ~−20 mV, L-glutamate elicited a more robust transport component and therefore its measured reversal potential was ~−3 mV. Various compounds were tested and a characteristic rank order for reversal potential (more negative to less negative) was found: L-aspartate>PDC>L-$\alpha$-aminoadipate>L-glutamate>L-quisqualate.

These data demonstrated that the EAAT4 transporter is capable of mediating both 1) the uptake of excitatory amino acids such as glutamate and aspartate, and 2) a substrate-gated increase in chloride conductance. Various substrates can be more or less effective as either amino acid uptake inhibitors or as elicitors of chloride conductance. Thus, the pharmacology of the two functions are separable and therefore subject to selective interventions, i.e., compounds that selectively inhibit or stimulate chloride ion conductance without affecting excitatory amino acid uptake.

The physiological significance of the large chloride conductance of EAAT4 is unknown; but like the chloride conductance gated by GABA-A receptors, it may have a general inhibitory affect on neurotransmission. It may therefore be therapeutically beneficial to selectively stimulate or inhibit the EAAT4 chloride conductance in diseases such as epilepsy, excitotoxicity, and neurodegenerative diseases. The separability of the two biochemical functions of amino acid uptake and chloride ion conductance in the EAAT4 provides an assay for detecting and identifying compounds that inhibit or stimulate the chloride ion conductance of the EAAT4 transporter but do not affect amino acid uptake. Such compounds are advantageous, due to the recognized hazards of pharmaceutical agents that inhibit amino acid uptake in the brain. The assays described herein provide a method for screening for agents that can selectively inhibit or stimulate chloride conductance without the risk of brain injury associated with concommitant inhibition of amino acid uptake.

Briefly, such assays are performed as follows, using voltage-clamped oocytes expressing EAAT4 as described above. First, the compounds are tested for the ability to elicit a current in the voltage-clamped, EAAT4expressing oocytes. If the compound does not elicit a current, the compound is then co-applied to the oocytes in the presence of L-aspartate to determine whether the compound is an inhibitor of the aspartate-elicited current. If the tested compound elicits a current, the relationship between the elicited current and the voltage is determined (as shown in FIGS. 6 and 7). This analysis yields the relative current amplitude, the reversal potential and the degree of rectification caused by treatment of the oocyte with the test compound. As described above, the reversal potential and degree of rectification reflect the relative contributions of the uptake-elicited current and the chloride conductance in the response of the oocyte to the test compound.

Compounds which elicit a current which is determined to have a significant chloride conductance component are then tested for their effect on excitatory amino acid uptake. Manmmalian cells or oocytes are treated with detectably-labeled L-aspartate and L-glutamate in the presence or absence of a compound to be tested. Compounds having little effect on excitatory amino acid uptake, particularly L-glutamate uptake, are thereby advantageously distinguished.

EXAMPLE 4
Construction of Fusion Proteins-Recombinant Expression Constructs for Expression of Immunologically—Active Epitopes of Amino Acid Transporters The EAAT4 amino acid transporter protein of the invention are expressed as fusion proteins in bacteria to produce immunologically-active epitopes. In these experiments, the amino acid transporter cDNAs of the invention are excised from their respective pOTV-containing constructs and subcloned into a pGEX-2T construct (Pharmacia, Piscataway, N.J.) whereby the coding sequences of the amino acid transporter cDNA is translationally in-frame with sequences encoding glutathione-S-transferase (described in Arriza et al., 1992, *J. Neurosci.* 12: 4045–4055), termed pGST-EAAT4 constructs. After introduction of the pGST-EAAT4 constructs into bacterial cells (*E. coli*, strain D5α) using conventional techniques (see Sambrook er al., ibid.), fusion protein expression is induced with isopropyl-1-thio-β-D-galactopyranoside as described (Smith & Johnson, 1988, *Gene* 67: 31–40) and purified using glutathione-Sepharose 4B (Phanmacia). Antibodies are then raised against the amino acid transporter of the invention by inoculation of rabbits with 300–500 μg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by inununoblotting using conventional techniques (Harlow & Lane, 1988, Antibodies: A Laboratory Manual, Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

What is claimed is:

1. An isolated polynucleotide encoding a human excitatory amino acid transporter wherein said polynucleotide hybridizes to a nucleic acid sequence encoding SEQ ID NO:2 at a temperature of 42° C. in a solution of 5×SSPE, 50% formamide, 7.5% Denhardt's solution, 2% SDS, and 100 Fg/ml denatured salmon sperm DNA.

2. An isolated polynucleotide according to claim 1, wherein hybridization is detected after washing in a solution of 2×SSPE/0.1% SDS at room temperature and in a solution of 0.1 ×SSPE/0.1% SDS at 50° C.

* * * * *